United States Patent
Haitjema et al.

(10) Patent No.: US 12,325,776 B2
(45) Date of Patent: Jun. 10, 2025

(54) BIODEGRADABLE, PHASE SEPARATED, THERMOPLASTIC MULTI-BLOCK COPOLYMER

(71) Applicant: InnoCore Technologies Holding B.V., Groningen (NL)

(72) Inventors: Henk Haitjema, Dedemsvaart (NL); Rob Steendam, Groningen (NL); Christine Hiemstra, Apeldoorn (NL); Johan Zuidema, Aduard (NL); Albert Doornbos, Groningen (NL); Thanh Nguyen, Eelderwolde (NL)

(73) Assignee: InnoCore Technologies Holding B.V., Groningen (NL)

( * ) Notice: Subject to any disclaimer, the term of this patent is extended or adjusted under 35 U.S.C. 154(b) by 501 days.

(21) Appl. No.: 17/765,389

(22) PCT Filed: Sep. 30, 2020

(86) PCT No.: PCT/NL2020/050606
§ 371 (c)(1),
(2) Date: Mar. 30, 2022

(87) PCT Pub. No.: WO2021/066650
PCT Pub. Date: Apr. 8, 2021

(65) Prior Publication Data
US 2022/0332900 A1   Oct. 20, 2022

(30) Foreign Application Priority Data
Oct. 1, 2019   (EP) .................................... 19200879

(51) Int. Cl.
*C08G 81/00* (2006.01)
*A61K 9/16* (2006.01)
(Continued)

(52) U.S. Cl.
CPC ............ *C08G 81/00* (2013.01); *A61K 9/1647* (2013.01); *A61K 9/5031* (2013.01); *C08G 63/08* (2013.01); *C08G 65/08* (2013.01); *C08G 2230/00* (2013.01)

(58) Field of Classification Search
CPC ...................................................... C08G 81/00
See application file for complete search history.

(56) References Cited

U.S. PATENT DOCUMENTS 6,339,130 B1 * 1/2002 Bennett ................ C08G 63/664
528/81
6,599,519 B1 * 7/2003 Seo ....................... A61K 9/1647
424/487
(Continued)

FOREIGN PATENT DOCUMENTS

DE   102006058755 A1   6/2008
WO   99/42147 A1   8/1999
(Continued)

OTHER PUBLICATIONS

International Search Report issued in PCT/NL2020/050606; mailed Dec. 9, 2020.
(Continued)

*Primary Examiner* — Michael L Leonard
(74) *Attorney, Agent, or Firm* — Studebaker Brackett PLLC

(57) ABSTRACT

The invention is directed to a biodegradable, phase separated, thermoplastic multi-block copolymer, a process for preparing a biodegradable, phase separated, thermoplastic multi-block copolymer, the use of a biodegradable, semi-crystalline, phase separated, thermoplastic multi-block copolymer, and a composition for the delivery of at least one biologically active compound to a host. The multi-block copolymer of the invention comprises at least one amor- (Continued)

phous hydrolysable pre-polymer (A) segment and at least one semi-crystalline hydrolysable pre-polymer (B) segment, wherein said multi-block copolymer under physiological conditions has a $T_g$ of 37° C. or less and a $T_m$ of 50-110° C.;
the segments are linked by a multifunctional chain extender;
the segments are randomly distributed over the polymer chain; and
the pre-polymer (B) segment comprises a X-Y-X triblock, wherein Y is a polymerisation initiator and X is a poly(p-dioxanone) segment with a block length expressed in p-dioxanone monomer units of 7 or more.

30 Claims, 13 Drawing Sheets

(51) Int. Cl.
*A61K 9/50* (2006.01)
*C08G 63/08* (2006.01)
*C08G 65/08* (2006.01)

(56) References Cited

U.S. PATENT DOCUMENTS

| | | | |
|---|---|---|---|
| 2003/0236319 A1* | 12/2003 | Yoon | A61L 17/105 523/122 |
| 2004/0007588 A1 | 1/2004 | Danby | |
| 2013/0272997 A1* | 10/2013 | Gray, Jr. | A61P 17/02 424/602 |
| 2014/0199385 A1 | 7/2014 | Steendam et al. | |
| 2017/0202996 A1* | 7/2017 | Andjelic | A61L 17/005 |

FOREIGN PATENT DOCUMENTS

| | | |
|---|---|---|
| WO | 2004/007588 A1 | 1/2004 |
| WO | 2013/015685 A1 | 1/2013 |

OTHER PUBLICATIONS

Written Opinion of the International Search Authority for PCT/NL2020/050606; mailed Dec. 9, 2020.

* cited by examiner

A

RCP 1710    RCP1718    RCP1714

B

A

B

BIODEGRADABLE, PHASE SEPARATED, THERMOPLASTIC MULTI-BLOCK COPOLYMER

BACKGROUND OF THE INVENTION

The invention is directed to a biodegradable, phase separated, thermoplastic multi-block copolymer, to a process for preparing a biodegradable, phase separated, thermoplastic multi-block copolymer, to the use of a biodegradable, semi-crystalline, phase separated, thermoplastic multi-block copolymer, and to a composition for the delivery of at least one biologically active compound to a host.

Peptides and proteins, together called polypeptides, play a vital role in all biological processes and have received a growing attention in recent years as drug candidates. The rapid advances in peptide and protein pharmacology along with the large-scale production of these compounds by recombinant DNA technology—among other techniques—have fueled enormous interest in these compounds. Unfortunately, peptide and protein development has far outpaced the ability to deliver these compounds systemically or locally using convenient and effective delivery systems.

Biodegradable polymers have received increased attention over the past decade for use in long-acting parenteral controlled release systems, either for systemic or site-specific drug delivery. Biodegradable controlled release formulations can significantly improve the pharmacokinetics of therapeutic compounds. This is especially relevant in the treatment of chronic diseases and for compounds with a narrow therapeutic window since systemic plasma concentrations can be reduced with concurrent reduction in undesirable side effects. Additionally, many new biologically active compounds have short half-lives, necessitating frequent injection to achieve therapeutically effective plasma levels. Patient compliance and the high costs associated with frequent dosing regimens for parenterally administered biologically active compounds have increased the interest in biodegradable parenteral sustained release dosage forms.

Poly(D,L-lactic acid) (PDLLA) and copolymers of lactic acid and glycolic acid, also known as PLGA copolymers, are the most widely applied biodegradable polymers for use in parenteral sustained release depot formulations. PLGA copolymers have been successfully used for the development of sustained release depot formulations for small molecules, such as risperidone, and therapeutic peptides such as leuprolide, goserelin or octreotide.

PLGA polymers have, however, several drawbacks that limit their use and make them less suitable for the delivery of polypeptides. Firstly, PLGA copolymers are relatively hydrophobic polymers and do not provide an optimal environment for encapsulated proteins. Proteins may adsorb to the polymer, resulting in slow and incomplete release, protein unfolding and/or aggregation. Secondly, the ability to manipulate the release of larger biologically active compounds such as an encapsulated polypeptide is limited since diffusion of such compounds through the relatively rigid and non-swellable PLGA matrices is negligible. The release of proteins from PLGA copolymers therefore depends on diffusion via pores present in the matrix and on the degradation of the matrix. Typically, the encapsulated protein remains entrapped in the polymer matrix until the moment the latter has degraded to such an extent that it loses its integrity or dissolves, resulting in biphasic or triphasic degradation-dependent release profiles typically obtained for PLGA-based depot formulations. Finally, during degradation of PLGA copolymers, acidic moieties are formed that accumulate in the rigid and non-swellable PLGA matrix resulting in the formation of an acidic micro-environment in the polymer matrix with in situ pHs that can be as low as 1-2. Under such acidic conditions encapsulated proteins may form aggregates leading to incomplete protein release. Moreover, the low pH may have a deleterious effect on the structural integrity and biological activity of the encapsulated peptide or protein, potentially leading to reduced therapeutic efficacy and enhanced immunogenicity. Chemical modification of proteins and peptides, such as acylation and adduct formation have been reported.

Thus, there is a need for biodegradable polymers that are more suitable for protein delivery. However, one of the advantages of PLGA and related polymers is that they have a proven track record of clinical use and are generally considered as highly biocompatible, and as a consequence and because of risk mitigation reasons, have been adopted by pharmaceutical companies to develop depot formulations for their active compounds. It is therefore desired that a new biodegradable polymeric protein delivery system would be designed of polymers that are composed of monomers that are well-known, biologically safe and clinically acceptable.

There remains a need in the art for further biodegradable, phase separated, thermoplastic multi-block copolymers. For example, the inventors found that multi-block copolymers containing a poly(L-lactide) crystalline block have a degradation time of 3-4 years. For the majority of sustained release drug delivery formulations, such a degradation time is undesirably long as it would lead to polymer accumulation upon repeated injection and could potentially induce long-term tolerability issues. It would be desirable to have a multi-block copolymer with a reduced degradation time relative to the multi-block copolymers containing a poly(L-lactide) crystalline block, such as a degradation time of approximately 0.5-1.5 years, depending on the duration of release. At the same time, it would be beneficial to retain the excellent tunability of the drug release kinetics of the multi-block copolymers containing a poly(L-lactide) crystalline block.

Poly(p-dioxanone) is a biodegradable polyester that is known for its excellent biocompatibility, biodegradability and mechanical flexibility. Poly(p-dioxanone) is semi-crystalline and exhibits a lower concentration of ester groups as compared to lactide- and glycolide-based polyesters, (Yang et al., *J. Macromol. Sci.-Pol. R.* 2002, 42(3), 373-398). Poly(p-dioxanone) exhibits a higher resistance to hydrolytic attack and degrades slower as compared to amorphous (co-)polyesters such as poly(D,L-lactide) and poly(D,L-lactide-co-glycolide) (Sabino et at, *Polym. Degrad. Stabil.* 2000, 69(2), 209-216; Hong et al., *J. Appl. Polym. Sci.* 2006, 102(1), 737-743; Lichun et al., *J. Biomedical Mat. Res.* 1999, 46(2), 236-244; Jie et al., *Polymer Int.* 1997, 42(4), 373; Fredericks et al., *J. Polym. Sci Pol. Phys.* 1984, 22(1), 57-66).

However, poly(p-dioxanone) is also known to be relatively hydrophilic as compared to lactide and glycolide-based polyesters. Based on the combination of (i) decreased concentration of ester groups (contributing to slower hydrolysis), (ii) increased hydrophilicity (contributing to faster hydrolysis) and (iii) use of low molecular weight pre-polymer blocks in multi-block copolymers, it is extremely challenging to predict how the degradation rate of multi-block copolymers composed of a low molecular weight crystalline poly(p-dioxanone) blocks would compare to the degradation kinetics of multi-block copolymers composed of low molecular weight crystalline poly(L-lactide) blocks.

Also, the use of poly(p-dioxanone), (PPDO), as a crystalline block in multi-block copolymers was disadvantageous as was previously reported by the inventors (WO-A-2013/015685). Synthesis of multi-block copolymers where the crystallisable segment is based on PPDO is hampered by the limited polymerisation of p-dioxanone monomer, and the limited solubility of PPDO in common solvents. The limited solubility of PPDO containing polymers also limits their use for preparation of controlled release formulations. Furthermore, according to WO-A-2013/015685 crystallisation of PPDO was expected to be slow and incomplete at fast cooling rates and/or low PPDO molecular weight, due to which preparation of microspheres via solvent extraction/evaporation based micro-encapsulation processes using multi-block copolymers with short PPDO blocks as segment B is not feasible.

Objective of the invention is to fulfil the above-mentioned need in the art and/or to overcome one or more of the drawbacks observed in the prior art.

SUMMARY OF THE INVENTION

The inventors surprisingly found that one or more of these objectives can be met, at least in part, when a pre-polymer (B) segment is used that contains poly(p-dioxanone) and has a specified block length.

Accordingly, in a first aspect the invention is directed to a biodegradable, phase separated, thermoplastic multi-block copolymer comprising at least one amorphous hydrolysable pre-polymer (A) segment and at least one semi-crystalline hydrolysable pre-polymer (B) segment, wherein said multi-block copolymer under physiological conditions has a $T_g$ of 37° C. or less and a $T_m$ of 50-110° C.;
the segments are linked by a multifunctional chain extender;
the segments are randomly distributed over the polymer chain; and
the pre-polymer (B) segment comprises a X-Y-X tri-block copolymer,
wherein
Y is a polymerisation initiator, and
X is a poly(p-dioxanone) segment with a block length expressed in p-dioxanone monomer units of 7 or more.

In a further aspect, the invention is directed to a process for preparing a biodegradable, phase separated, thermoplastic multi-block copolymer according to the invention, comprising
i) performing a chain extension reaction of pre-polymer (A) and pre-polymer (B) in the presence of a multifunctional chain-extender, wherein pre-polymer (A) and (B) are both diol or diacid terminated and the chain-extender is di-carboxylic acid, diisocyanate, or diol terminated; or
ii) performing a chain extension reaction using a coupling agent, wherein pre-polymer (A) and (B) are both diol or diacid terminated and the coupling agent is preferably dicyclohexyl carbodiimide.
wherein the pre-polymer (B) segment comprises a X-Y-X tri-block copolymer, wherein
Y is a polymerisation initiator, and
X is a poly(p-dioxanone) segment with a block length expressed in p-dioxanone monomer units of 7 or more.

In yet a further aspect, the invention is directed to the use of a biodegradable, semi-crystalline, phase separated, thermoplastic multi-block copolymer according to the invention for drug delivery, preferably in the form of microspheres, microparticles, nanoparticles, nanospheres, rods, implants, gels, coatings, films, sheets, sprays, tubes, membranes, meshes, fibres, or plugs.

In yet a further aspect, the invention is directed to a composition for the delivery of at least one biologically active compound to a host, comprising at least one biologically active compound encapsulated in a matrix, wherein said matrix comprises at least one biodegradable, semi-crystalline, phase separated, thermoplastic multi-block copolymer according to the invention.

[poly(p-dioxanone)] multi-block copolymers with a block ratio of 10/90. Release is shown as μg peptide released in time.

Figure 14:
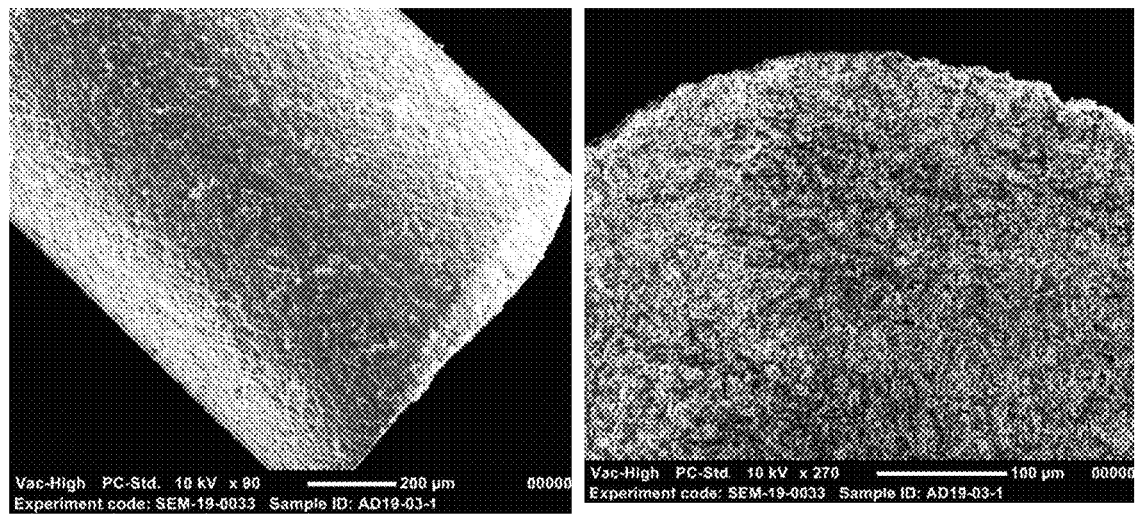
Figure 14:
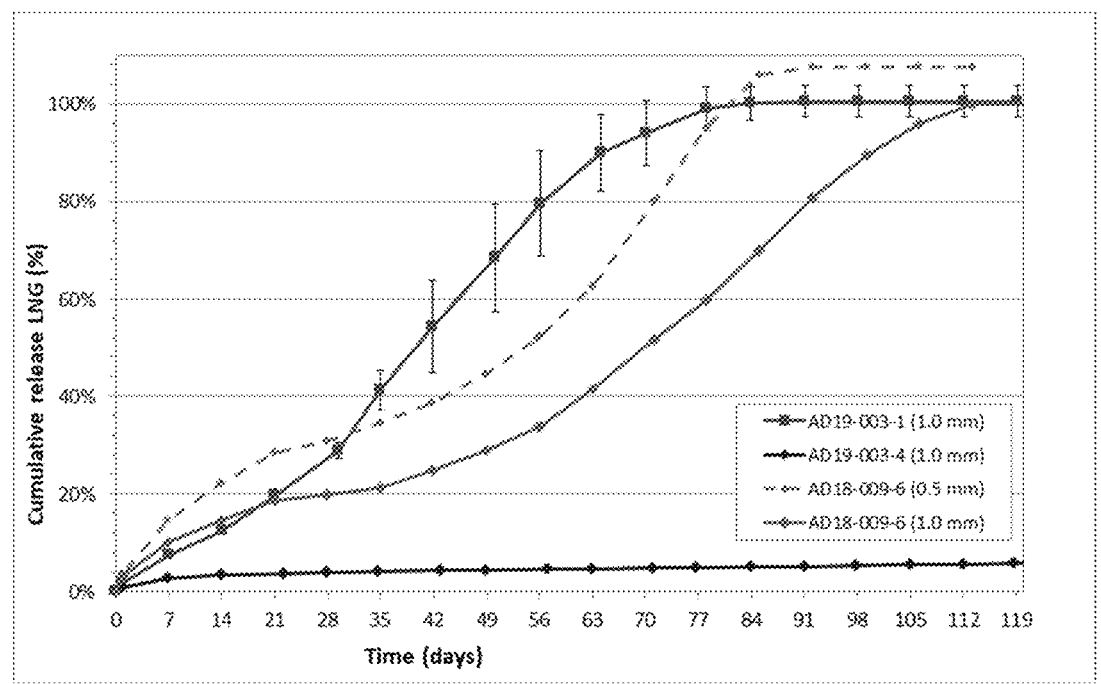

FIG. 14 SEM images (AD19-003-1 (1.0 mm)) (panel A) and cumulative in vitro release of hot melt extruded levonogestrel implants prepared of different (multi-block) copolymers (panel B),

DETAILED DESCRIPTION OF THE INVENTION

The multi-block copolymer of the invention can be composed of at least two different segments each having different physical characteristics, including degradation and swelling characteristics. Due to their unique make-up and their semi-crystalline phase separated morphology, the materials of the invention are surprisingly versatile and extremely suited for constructing drug delivery matrices and drug eluting coating, which are utilisable for encapsulating certain therapeutic agents and for sustained release of the encapsulated therapeutic agent either locally or into the systemic circulation. A composition comprising a biodegradable, phase separated, thermoplastic multi-block copolymer matrix of the invention is of particular interest for the sustained release of a biologically active compound, such as a small molecule or a biologically active polypeptide to a host. Additionally, the multi-block copolymer of the invention degrades relatively fast as compared to water-swellable phase-separated polymers disclosed in WO-A-2013/015685.

In the art, the synthesis of multi-block copolymers where the crystallisable segment is based on poly(p-dioxanone) is reported as being hampered by the limited polymerisation of the monomer, p-dioxanone and the limited solubility of poly(p-dioxanone) in common solvents. As mentioned, for instance, in WO-A-2013/015685, typically this leads to a maximum conversion of approximately 80%, whereas monomers such as lactide and glycolide can be easily polymerised to conversions above 95%.

The synthesis of the pre-polymer comprising poly(p-dioxanone) is quite challenging as already early in the polymerisation process the reaction mixture typically turns solid due to crystallising poly(p-dioxanone). This means that at that stage, reaction mixture stirring has seized, and propagation can only take place in the liquid areas where the dissolved monomer is located, in the midst of a matrix of crystallised poly(p-dioxanone).

The inventors realised that this also means that conversion checking must be done carefully, since the p-dioxanone monomer easily sublimates and leaves the polymerising reaction mixture, hence suggesting a high conversion when a lot of monomer has sublimated. Using careful management of the poly(p-dioxanone) synthesis, the inventors were able to attain conversions of >90% with a control over the poly(p-dioxanone) block molecular weight of ±one monomer unit. This also means that the resulting monomer content of the resultant poly(p-dioxanone) block is typically 10-20% by total weight of the poly(p-dioxanone) block. However, the inventors found that in the multi-block copolymer synthesis the monomer does not interfere in the chain extension reaction. The control over p-dioxanone conversion also allows a control of molecular weight. The inventors further realised that control of the precise poly(p-dioxanone) block length can be gained by anticipating the actual conversion in the target poly(p-dioxanone) block length. Because of an overestimation, being the assumption of the 80-90% conversion, the inventors were able to set the exact block length. For example, starting with 27 monomers and having 85% conversion results in an X-block of (27/2× 0.85=) 11.5 monomers. At 80% conversion, this results in an X-block of (27/2×0.80=) 11 monomers. At 90% conversion, this results in an X-block of (27/2×0.90=) 12 monomers.

p-Dioxane is chosen as the solvent of choice for the chain extension reaction because of its compatibility with the used chain extender/$Sn(Oct)_2$ combination. From our data it is also shown that p-dioxane can easily be removed from the polymers, for its relatively low boiling point and reasonable volatility, at temperatures which pose no risk to the integrity of the polymers. Possible solvent alternatives for chain extension, like dimethyl sulphoxide (DMSO) or dimethyl acetamide (DMAc) are much less attractive because boiling points are high and hence are much more difficult to remove from the polymers, giving rise to possible issues with polymer stability and biological acceptability. Although p-dioxane is described as a non-solvent for poly(p-dioxanone) (Yang et al., *J. Macromol. Sci.-Pol. R.* 2002, 42(3), 373-398; Kim et al., *J. Chem. Eng. Data* 2006, 51(4), 1182-1184), solubility is sufficient in combination with the low molecular weights of the current polymers.

The term "phase-separated" as used herein is meant to refer to a system, in particular a copolymer, built of two or more different pre-polymers, of which at least two are (partially) incompatible with each other at body temperature (under physiological conditions such as in the human body). Thus, the pre-polymers do not form a homogeneous mixture when combined, neither when combined as a physical mixture of the pre-polymers, nor when the pre-polymers are combined in a single chemical species as "chemical mixture", viz, as copolymer.

The term "pre-polymer" as used herein is meant to refer to the polymer segments that are randomly linked by a multi-functional chain extender, together making up the multi-block copolymer of the invention. Each pre-polymer may be obtained by polymerisation of suitable monomers, which monomers thus are the chemical units of each pre-polymer. The desired properties of the pre-polymers and, by consequence, of the multi-block copolymer of the invention, can be controlled by choosing a pre-polymer of a suitable composition and molecular weight (in particular $M_n$), such that the required $T_m$ or $T_g$ is obtained.

The terms "block" and "segment" as used herein are meant to refer to distinct regions in a multi-block copolymer. The terms block and segment are used interchangeably.

The term "multi-block" as used herein is meant to refer to the presence of at least two distinct pre-polymer segments in a polymer chain.

The term "thermoplastic" as used herein is meant to refer to the non-cross-linked nature of the multi-block copolymer. Upon heating, a thermoplastic polymer becomes fluid, whereas it solidifies upon (re-)cooling. Thermoplastic polymers are soluble in proper solvents.

The term "hydrolysable" as used herein is meant to refer to the ability of reacting with water upon which the molecule is cleaved. Hydrolysable groups include ester, carbonate, phosphazene, amide and urethane groups. Under physiological conditions, only ester, carbonate and phosphazene groups react with water in a reasonable time scale.

The term "multifunctional chain-extender" as used herein is meant to refer to the presence of at least two reactive groups on the chain-extender that allow chemically linking reactive pre-polymers thereby forming a multi-block copolymer.

The term "random multi-block copolymer" as used herein is meant to refer to a multi-block copolymer where the distinct segments are distributed randomly over the polymer chain.

The term "water-soluble polymer" as used herein is meant to refer to a polymer that has a good solubility in an aqueous medium, such as water, under physiological conditions. This polymer, when copolymerised with more hydrophobic moieties, renders the resulting copolymer swellable in water. The water-soluble polymer can be a diol, a diamine or a diacid. The diol or diacid is suitably used to initiate the ring-opening polymerisation of cyclic monomers.

The term "swellable" as used herein is meant to refer to the uptake of water by the polymer. The swelling ratio can be calculated by dividing the mass of the water-swollen copolymer by that of the dry copolymer.

The term "semi-crystalline" as used herein is meant to refer to a morphology of the multi-block copolymer that comprises two distinctive phases, an amorphous phase and a crystalline phase. In one embodiment, the multi-block copolymer is made up of an amorphous phase and a crystalline phase.

The term "biologically active compound" as used herein is intended to be broadly interpreted as any agent that provides a therapeutic or prophylactic effect. Such agents include, but are not limited to, antimicrobial agents (including antibacterial and antifungal agents), anti-viral agents, anti-tumour agents, hormones and immunogenic agents.

The term "biologically active polypeptide" as used herein is meant to refer to peptides and proteins that are biologically active in a mammal body, more in particular in the human body.

The inventors surprisingly found that the multi-block copolymers of the invention, which comprise poly(p-dioxanone) in the pre-polymer (B) segment, have a desirable degradation time which allows a favourable release of proteins and/or polypeptides. At the same time, the degradation products of the multi-block copolymers do not, or significantly less, lead to degradation of the peptide or protein. Hence, the biologically active compounds and their functionalities remain (or mainly remain) intact.

The multi-block copolymers of the invention have a $T_m$ of 50-110° C. under physiological conditions, such as in the range of 60-110° C., in the range of 60-100° C., in the range of 70-100° C., or in the range of 70-90° C. This is due to the pre-polymer (B) segment. The (B) segment comprises 70% or more by total weight of said pre-polymer (B) segment of polyp-dioxanone); in another embodiment the (B) segment comprises 80% or more, 85% or more, 90% or more, or 95% or more by total weight of said pre-polymer (B) segment of poly(p-dioxanone). In one embodiment, the (B) segment is based on a pre-polymer consisting of poly(p-dioxanone). The amorphous phase of the phase separated multi-block copolymers of the invention predominantly consists of the soft (A) segments. Surprisingly, the inventors have found that the amorphous part of the hard (B) segments also contributes to the total amorphous phase of the multi-block copolymers of this invention.

In accordance with the invention, pre-polymer (B) segment comprises poly(p-dioxanone). The pre-polymer (B) segment can additionally comprise further monomer units such as ε-caprolactone and/or δ-valerolactone.

The pre-polymer (B) segment comprises an X-Y-X tri-block copolymer, wherein Y is a polymerisation initiator and X is a poly(p-dioxanone) segment. The block length of the poly(p-dioxanone) segment X expressed in terms of p-dioxanone monomer units is 7 or more. Suitably, the block length of the poly(p-dioxanone) segment X can be 7-35 p-dioxanone monomer units, such as 7-30 p-dioxanone monomer units, 8-25 p-dioxanone monomer units, 9-20 p-dioxanone monomer units, 10-15 p-dioxanone monomer units, or 11-14 p-dioxanone monomer units.

Hence, the pre-polymer (B) segment can comprise an X-Y-X tri-block copolymer wherein each poly(p-dioxanone) segment X has a block length expressing in terms of p-dioxanone monomer units of 7 or more.

In an embodiment, the pre-polymer (B) segment consists of a X-Y-X tri-block copolymer.

The polymerisation initiator Y in the X-Y-X tri-block copolymer can suitably be a diol, such as an aliphatic diol with 2 to 8 carbon atoms. Examples of suitably aliphatic diols to be used as polymerisation initiator Y include ethylene glycol, 1,2-propanediol, 1,3-propanediol, 1,4-butanediol, 1,3-butanediol, 2,3-butanediol, diethylene glycol, dipropylene glycol, triethylene glycol, poly(ethylene glycol), 1,5-pentanediol, 1,6-hexanediol, neopentyl glycol, hydrogenated bisphenol A, and glycerol. Preferred polymerisation initiators include ethylene glycol, 1,2-propanediol, 1,3-propanediol, 1,4-butanediol, 1,3-butanediol, 2,3-butanediol, 1,5-pentanediol, and 1,6-hexanediol. More preferred polymerisation initiators include ethylene glycol, 1,4-butanediol and 1,6-hexanediol. In one embodiment, the polymerisation initiator is 1,4-butanediol.

If the block length of the pre-polymer (B) segment is too small, then the melting enthalpy is too low and crystallisation of the polymer matrix during extraction of dichloromethane is too low/slow which results in too slow hardening of the microspheres, which leads to agglomeration and smearing and/or sticking of the microparticles during production and a microparticle dry powder with a very broad particle size distribution. Additionally, a small pre-polymer (B) segment can lead to incomplete crystallisation. This gives rise to an instable product, as further crystallisation can take place during storage, thereby changing the critical properties of the product (such as the release rate).

Pre-polymer (B) segments can suitably have a molecular weight distribution ($M_w/M_n$) of 1.0 or more, such as 1.1, or more, 1.2 or more, 1.3 or more, or 1.4 or more. The molecular weight distribution of pre-polymer (B) segments is in one embodiment 3.0 or less. In another embodiment, the molecular weight distribution of pre-polymer (B) segments is 2.0 or less, such as 1.8 or less, 1.6 or less, 1.5 or less, or 1.4 or less. If the molecular weight distribution of pre-polymer (B) segments becomes high, the crystallisability of the multi-block copolymers is adversely affected. In turn, this means that such multi-block copolymers are less suitable for preparing microspheres.

The pre-polymer (B) segments can further have a density (as measured according to ASTM D1506) of 1.1 g/cm³ or more, such as 1.15 g/cm³ or more, or 1.2 g/cm³ or more. The density of pre-polymer (B) can be 1.5 g/cm³ or less, such as 1.45 g/cm³ or less, or 1.4 g/cm³ or less. The melt flow index of pre-polymer (B) segment (as measured at 150° C. with a load of 2.16 kg according to ASTM D1238-86) can be 0.1 g/10 min or more, such as 0.2 g/10 min or more, or 0.3 g/10 min. The melt flow index of pre-polymer (B) (as measured at 150° C. with a load of 2.16 kg according to ASTM D 1238-86) can be 7 g/10 min or less, such as 6 g/10 min or less, or 5 g/10 min or less.

The hard pre-polymer (B) segment of the multi-block copolymer of the invention is typically semi-crystalline, i.e. partly amorphous. The amorphous part of the hard (B) segments will (partly) phase mix with the soft (A) segments and thus both will contribute to the overall $T_g$ of the multi-block copolymer. Therefore, the $T_g$ of the amorphous phase is determined by both the $T_g$ of segment (A) and the $T_g$ of segment (B), in combination with the molar ratio of segment (A)/segment (B). The $T_g$ can be varied from $T_g$ close to the $T_g$ of pre-polymer (A) (when a ratio of pre-polymer (A) to pre-polymer (B) of close to one is used) to $T_g$ close to the $T_g$ of pre-polymer (B) (when a ratio of pre-polymer (A) to pre-polymer (B) of close to zero is used). Importantly, the release of actives encapsulated in the polymer matrix depends heavily on the $T_g$ of the amorphous phases, as the diffusion of actives occurs through the amorphous phase and not through the dense, crystalline phase. Also, the degradation rate of a polymer depends heavily on the $T_g$ of the amorphous phase, as this influences the rate of water influx and thus the rate of hydrolysis.

The multi-block copolymers of the invention allow the preparation of non-sticky microspheres by various processes including solvent-extraction/evaporation based on emulsification processes such as oil-in-water (O/W), water-in-oil-in-water (W/O/W), solid-in-oil-in-water (S/O/W), water-in-oil-in-oil (W/O/O), or solid-in-oil-in-oil (S/O/O) emulsions. The minimum length of the crystallisable pre-polymer (B) segment plays an important role in obtaining multi-block copolymers that combine good product stability with good processability. Proper microspheres cannot be made using multi-block copolymers where the pre-polymer (B) segment comprises a X-Y-X triblock copolymer where X is composed of a short poly(p-dioxanone) block, since the short poly(p-dioxanone) blocks do not sufficiently crystallise and/or crystallise very slowly. Such an incompletely crystallised polymer is instable upon storage as further crystallisation may occur. This in turn changes the critical properties of the polymer. Additionally, short pre-polymer (B) segments give rise to sticky polymers which are difficulties during processing such as agglomerate and fusing together of microspheres during the extraction/evaporation process step.

The multi-block copolymers of the invention furthermore allow the preparation of solid drug delivery implants via hot melt extrusion. Contrary to semi-crystalline multi-block copolymers containing a crystalline PLLA blocks with high melting temperatures, such as 50[PCL-PEG1500-PCL]-b-[PLLA], which require high extrusion temperatures of up to or even above 130° C., multi-block copolymers containing crystalline PPDO blocks can be extruded at relatively low melting temperatures as low as 80° C. which is favourable for the preservation of the integrity of labile molecules and polypeptide-based active ingredients.

The multi-block copolymers of the invention in one embodiment comprise segments derived from a water-soluble polymer (such as hydrophilic PEG segments). The presence of such segments promotes swelling of the phase separated multi-block copolymers in an aqueous environment to form a swollen hydrogel providing a natural environment for biologically active compounds such as proteins. When the multi-block copolymers of the invention are applied as a polymer matrix in a controlled release formulation for delivering a biologically active compound, the swellability of the multi-block copolymers can avoid accumulation in the polymer matrix of acidic degradation products formed during hydrolysis of the polymer chains. Instead, such degradation products are released from the matrix and thereby prevent the formation of an acidic micro-environment in the polymer matrix that could be deleterious to the encapsulated biologically active compound. Moreover, swellability of the phase separated multi-block copolymers allows gradual release of any encapsulated compounds by diffusion. The biphasic or triphasic release patterns typically obtained for non-swellable biodegradable polyesters such as poly(D,L-lactide) or poly(lactic-co-glycolic acid) are thereby avoided.

In the multi-block copolymers of the invention, the content of segments derived from a water-soluble polymer may be varied independently from the block length of the pre-polymer (B) segment (crystalline segment). Therefore, high contents of segments that are derived from a water-soluble polymer can be obtained, while maintaining crystallinity. Furthermore, the intrinsic viscosity (IV) of the multi-block copolymers of the invention may be varied independently from the composition. The high degree of variability of the multi-block copolymers of the invention allows easy tuning of the length, ratio and composition of the segments to obtain the desired degradation characteristics and drug release kinetics.

The multi-block copolymers of this invention further have advantages over block copolymers of structure ABA as disclosed by Kissel et al. (*J. Contr. Rel.* 1996, 39(2), 315-326). These block copolymers contain hydrophilic poly(ethylene oxide) B blocks and hydrophobic, biodegradable poly(D,L-lactide-co-glycolide) A blocks (poly(D,L-lactide-co-glycolide)-poly(ethylene glycol)-poly(D,L lactide-co-glycolide). Although polymer properties can be greatly improved by using block copolymers with blocks of different copolymers instead of homo or random copolymers, these ABA copolymers still have certain disadvantages.

Typically ABA copolymers should have a certain minimum molecular weight to assure that critical quality attributes such as e.g. mechanical rigidity, processability or thermal stability are met. To obtain a a certain minimum molecular weight of the ABA copolymer, the sequences A and B must have a certain length. The blocks may independently behave as the individual homopolymers with similar composition. Properties of the ABA type copolymers can only be tuned by varying the composition of A and B blocks. Another disadvantage is that block copolymers must be prepared at relatively high temperatures (>100° C.) under inert conditions for complete conversion of all the monomers and to obtain sufficient molecular weight. The first disadvantage can be solved by using multi-block copolymers wherein the blocks or segments are much shorter and linked together by a chemical reaction performed at temperatures below 100° C. Properties such as degradation behaviour can be tuned in a much better way by choosing the proper combination of segment lengths, ratio and composition.

Furthermore, due to the relatively high temperatures used in the process of preparing ABA block copolymers (and derivatives thereof), there is always a possibility of transesterification, resulting in a certain extent of phase mixing. The multi-block copolymers of the invention do not suffer from this disadvantage since they can be prepared by linking pre-polymers with previously determined monomer composition at rather low temperatures (<100° C.) thus avoiding transesterification and other side-reactions reactions, which may cause the generation of undesired degradation and other by-products. This means that the monomer sequence length of the copolymer is determined by the choice of building components and not so much by reaction time and temperature, as being usually applied for synthesis of random copolymers. Another advantage of multi-block copolymers of this invention prepared by linking of pre-polymers using a multifunctional chain-extender is that the pre-polymer segments are randomly distributed in the copolymer, thus offering much more possibilities of tuning the properties. A random multi-block copolymer is for example ABBBBA- BAAABBAAAAA . . . etc. The random multi-block copolymers of the invention provide many advantages that cannot be obtained with alternating multi-block copolymers.

Firstly, the random multi-block copolymers obtained by chain extension of A and B blocks have an unlimited A to B ratio. A:B can, for instance, be 10:90, but may as well be 90:10. In contrast, the ratio of the blocks in an alternating multi-block copolymer is limited to the ratio used in the chain extended polymer. For instance, in the case of chain extension of AB the A:B ratio in the multi-block copolymer is 50:50. The random nature of the multi-block copolymers of the invention greatly increases the possible compositions of the material and thereby the control over its physical and chemical properties. This includes a better control of the swelling capacity in water, morphology (phase separation, amorphous/crystallinity) and polymer degradation.

Secondly, the synthesis method of the random multi-block copolymers of the invention is significantly less laborious as compared to the synthesis of alternating multi-block copolymers. In alternating multi-block copolymers either segments A and B in case of AB di-blocks, or segments A and C in case of ACA tri-blocks, have to be linked prior to chain-extension (or a macro chain-extender needs to be synthesised). In random multi-block copolymers, separate A and B blocks do not have to be linked prior to chain extension but are directly chain extended with a chain-extender.

Another advantage of the multi-block copolymers of the invention is that they are based on a multifunctional (such as an aliphatic) chain-extender. By choosing the type and amount of chain-extender the polymers properties can be affected (for instance, the chain-extender may act as a softener or it may affect the degree of phase separation). The total degree of freedom to obtain polymers with the desired properties is very high.

The phase separated multi-block copolymers of the invention can swell sufficiently in an aqueous environment and under physiological conditions upon administration so as to provide an aqueous microenvironment for the encapsulated peptide or protein and allow diffusion-controlled release of the peptides and proteins. The materials thus show a significant decrease of the mechanical strength. Although such materials can be used as shape-memory materials under dry conditions without showing a significant decrease in mechanical strength prior to the transition to the memorised shape, e.g. by means of using temperature or light as an external trigger, these materials do show significant dimensional changes and a significant decrease of their mechanical strength under hydrated conditions, simply because these materials absorb significant amounts of water due to their hydrophilic character leading to extensive swelling and plasticisation of the material. As a consequence, under hydrated conditions, such as the physiological conditions encountered in a human or animal body, the size of constructs prepared of these materials changes significantly and the mechanical properties of these materials change orders of magnitude. Contrary to the multi-block copolymers of the current invention, the shape-memory materials described in U.S. Pat. No. 5,711,958 hardly swell under hydrated conditions, such as the physiological conditions encountered in a human or animal body.

Phase separated polyesters or polyester-carbonates of this invention are a promising group of biomaterials and can be used in various drug delivery applications since they provide excellent control over drug release and allow release of biologically active compounds, such as polypeptides.

The morphology of the multi-block copolymer (or of a construct made thereof) is dependent on the environmental conditions: a DSC (Differential Scanning Calorimetry) measurement may be performed under inert (dry) conditions and the results may be used to determine the dry materials thermal properties. However, the morphology and properties under physiological conditions (i.e., in the body) may be different from the morphology and properties under ambient conditions (dry, room temperature). It is to be understood that the transition temperatures, $T_g$ and $T_m$ as used herein, refer to the corresponding values of a material when applied in, vivo; viz when at equilibrium with an aqueous environment or an atmosphere that is saturated with water vapour at body temperature. This may be simulated in vitro by performing the DSC measurement after allowing the material to equilibrate with a water-saturated atmosphere. When in dry state, the materials used in the invention may have $T_g$ values that are somewhat higher than at mammalian body conditions, that is to say, when the dry materials are subjected to DSC, the first inflection point may arise at higher temperatures, for instance at 42° C., 50° C., or more. Upon application in vivo; however, the dry material's $T_g$ and/or $T_m$ will drop as a result of the absorption of water, which plasticises the polymer and this final $T_g$ should be around body temperature or lower according to the invention. The final $T_m$ should be present at temperatures between 50° C. and 110° C. under physiological conditions.

For instance, a polymer that contains PEG in the soft pre-polymer (A) segment can be crystalline under dry conditions at ambient temperature, while amorphous under wet conditions, giving a mixed $T_g$ or two separated $T_g$s of the soft pre-polymer (A) segment. The phase separated character of the copolymers of the invention is reflected in the profile of the $T_g$ or $T_m$. The phase separated copolymers are characterised by at least two phase transitions, each of which is related to (but in general not identical to) the corresponding $T_g$ or $T_m$ values of the pre-polymers which are comprised in the copolymer. The $T_g$ is determined by taking the midpoint of the specific heat jump, as may be measured e.g. by DSC. The $T_m$ is the peak maximum of the melting peak. As defined herein, values of $T_g$ and $T_m$ of a certain pre-polymer reflect the values as measured on the copolymer. In case of complete immiscibility of the pre-polymers, the $T_g$ of the copolymer is governed solely by the $T_g$ of the amorphous, soft pre-polymer (A). In practice, however, the composition of the crystalline and amorphous phase of the multi-block copolymer is not the same as the composition of the soft pre-polymer (A) segments and the semi-crystalline pre-polymer (B) segments. The amorphous part of the original hard segment forming pre-polymer will mix with the soft segment forming pre-polymer (A) and thus become part of the amorphous phase. The $T_g$ value of the amorphous phase is then different from that of the pre-polymer used. The extent of miscibility (and therefore the deviation of $T_g$ and/or $T_m$ from those of the corresponding pre-polymers) is dependent on the pre-polymer composition, ratio and segment length in the copolymer. The $T_g$ of the copolymer segments generally lies between the $T_g$ value of the phase mixed copolymer and the $T_g$ value of the separate pre-polymers.

The physicochemical properties (such as degradation, swelling and thermal properties) of the multi-block copolymers can be easily tuned by changing the type of monomers of the soft and hard segment forming pre-polymers and their chain length and chain ratio and by choosing the type and amount of chain-extender. Furthermore, the phase transition temperatures are low enough for processing the polymer in the melt. The monomer ratio and distribution of the copolymer can be easily controlled by varying the polymerisation conditions.

A crystalline pre-polymer (B) segment is usually desired to obtain non-sticky materials. Also, the phase separated morphology, with amorphous and crystalline domains, must be maintained during exposure to physiological conditions (i.e. an aqueous environment at body temperature) in order to have controlled swelling of the polymer matrix. Control over the swelling degree is essential to control the release of encapsulated compounds. The crystalline pre-polymer (B) segments act as physical cross-links that control the swelling of the more hydrophilic soft pre-polymer (A) segments. Besides being affected by the content of hard pre-polymer (B) segment, the swelling degree of the polymers also depends on the content and molecular weight/length of water-soluble polymer in the soft pre-polymer (A) segment.

A prerequisite of the phase separated segmented multi-block copolymers is that they have a $T_m$ in the range of 50-110° C. and a $T_g$ of 37° C. or less under physiological conditions. This may be obtained by using a pre-polymer (B) with a $T_m$ in the range of 50-110° C. under physiological conditions and a pre-polymer (A) with a $T_g$ of 37° C. or less under physiological conditions. Pre-polymer (B) can, for instance, have a $T_m$ in the range of 60-110° C. under physiological conditions, such as in the range of 60-100° C., in the range of 70-100° C., or in the range of 75-95° C. The $T_m$ of the pre-polymer (B) segment in the multi-block copolymer can be lower than that of the non-reacted pre-polymer (B) due to decreased chain flexibility once the pre-polymer is built in in the multi-block copolymer and due to possible phase mixing of other components of the multi-block copolymer in the crystalline phase. Pre-polymer (A) may, for instance, have a $T_g$ of 30° C. or less under physiological conditions, such as 25° C. or less, 15° C. or less, or ° C. or less. The pre-polymer (B) can have a $T_g$ of 0° C. or less. In one embodiment the pre-polymer (B) can have a $T_g$ of –20° C. or less, –25° C. or less, –30° C. or less, –35° C. or less, or –40° C. or less.

Generally, the desired phase separated morphology (reflected by one $T_m$ and at least one low $T_g$ value) may be obtained by varying the composition, e.g. by choosing the number average molecular weight, $M_n$, of pre-polymer (A) and pre-polymer (B). It is also possible to influence the phase separated morphology by varying the segment A/segment B ratio.

The segmented multi-block copolymers of this invention comprise a soft pre-polymer (A) segment which is derived from pre-polymer (A). Pre-polymer (A) which is hydrolysable and typically completely amorphous at physiological (body) conditions. Furthermore, pre-polymer (A) in one embodiment has at least one phase transition being a $T_g$ of 37° C. or less, or in one embodiment 35° C. or less, 30° C. or less, or 25° C. or less, as measured under physiological (body) conditions. This segment will be part of the amorphous phase in the multi-block copolymer, wherein the amorphous phase is referred herein as phase (A). The copolymers of the invention also comprise a hard pre-polymer (B) segment which is derived from pre-polymer (B). Pre-polymer (B) comprises a semi-crystalline, hydrolysable polymer typically with a $T_m$ of 50-110° C. as measured at physiological (body) conditions. The pre-polymers (A) and (B) that form the "soft" and "hard" segments, respectively, are linked by a multifunctional chain-extender. Typically, the crystalline phase(s) is (are) comprised of hard pre-polymer (B) segments and the amorphous phase(s) is (are) comprised of soft pre-polymer (A) segments and the amorphous part of pre-polymer (B) segments. The crystalline and amorphous phase(s) is (are) incompatible or only partially compatible at body conditions, viz, they phase separate. The multifunctional chain-extender is in one embodiment an aliphatic molecule.

In a preferred embodiment, the resulting multi-block copolymers of the invention have a structure according to formula (1):

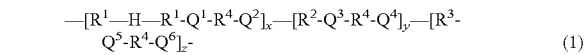

(1)

wherein $R^1$ is part of the pre-polymer (A) segment, which is part of phase (A), and may be amorphous polyester, amorphous polyetherester or amorphous polycarbonate; or an amorphous pre-polymer that is obtained from combined ester, ether and/or carbonate groups. H is the middle block of the pre-polymer (A) segment and is derived from a water-soluble polymer. The block derived from the water-soluble polymer may be amorphous or semi-crystalline at room temperature. However, block H thus introduced in the pre-polymer (A) segment will become amorphous at physiological conditions. This water-soluble polymer is selected from the group consisting of polyethers such as polyethylene glycol (PEG), polytetramethyleneoxide (PTMO) and polypropyleneglycol (PPG), polyvinylalcohol (PVA) polyvinylpyrrolidone (PVP), polyvinylcaprolactam, poly(hydroxyethylmethacrylate) (poly-(HEMA)), polyphosphazenes, or copolymers of the previous polymers. In one embodiment. H is PEG, which is the initiator of the ring-opening polymerisation of a cyclic monomer that forms $R^1$.

$R^2$ is the pre-polymer (B) segment and mainly or entirely contributes to phase (B). $R^2$ may be a crystalline or semi-crystalline polyester, polyetherester, polycarbonate or polyanhydride; or pre-polymers of combined ester, ether, anhydride and/or carbonate groups. It is possible that part of phase $R^2$ is amorphous, in which case this part of $R^2$ will contribute to phase (A). $R^1$ and $R^2$ are in one embodiment not the same. The variable z is zero or a positive integer. Variables x and y are both a positive integer.

Optionally, segment $R^3$ is present. This segment is derived from a water-soluble polymer that is chosen from the group of polymers mentioned for H. $R^3$ will be part of the amorphous phase (A) under physiological conditions. If $R^3$ is present, then the multi-block copolymer of the invention comprises a water-soluble polymer as an additional pre-polymer. In one embodiment, this water-soluble polymer is selected from the group consisting of polyethers such as polyethylene glycol (PEG), polytetramethyleneoxide (PTMO), polypropyleneglycol (PPG), polyvinylalcohol (PVA), polyvinylpyrrolidone (PVP), polyvinylcarprolactam, poly(hydroxymethylmethacrylate) (poly-(HEMA)), polyphosphazenes, polyorthoesters, polyorthoesteramides or copolymers of the previous polymers. For example, this additional water-soluble polymeric segment can be derived from PEG having a $M_n$ of 150-5000 g/mol. The additional pre-polymer that is derived from a water-soluble polymer can suitably be present in the multi-block copolymer in an amount of 60% or less by total weight of the multi-block copolymer, such as 50% or less, 40% or less, 30% or less, 20% or less, 10% or less, or 5% or less. The amount of the additional water-soluble polymer segment can be 0.1% or more by total weight of the multi-block copolymer, such as 1% or more, or 2% or more, 3% or more, 4% or more, or 5% or more.

$R^4$ is derived from the chain-extender and consists of an aliphatic $C_2$-$C_8$ alkylene group, optionally substituted by a $C_1$-$C_{10}$ alkylene, the aliphatic group being linear or cyclic. $R^4$ is in one embodiment a butylene. —$(CH_2)_4$—, group. The $C_1$-$C_{10}$ alkylene side group may contain protected S, N, P or O moieties. Chain-extenders containing aromatic groups are generally not suitable, since chain-extenders containing aromatic groups may give rise to undesired degradation products. Therefore, aliphatic chain-extenders are preferred.

$Q^1$-$Q^6$ are linking units obtained by the reaction of the pre-polymers with the multifunctional chain-extender. Each of $Q^1$-$Q^6$ may be independently selected from amine, urethane, amide, carbonate, ester and anhydride. The event that all linking groups Q are different is rare and usually not preferred.

Typically, one type of chain-extender may be used with three pre-polymers having the same end-groups resulting in a copolymer of formula (1) with six similar linking groups.

In case pre-polymers $R^1$ and $R^2$ are differently terminated, two types of groups Q will be present: e.g. $Q^1$ and $Q^2$ will be the same between two linked segments $R^1$, but $Q^1$ and $Q^2$ are different when $R^1$ and $R^2$ are linked. The examples of formula (1) show the result of the reaction with a difunctional chain-extender and difunctional pre-polymers.

With reference to formula (1) the polyesters of the invention may also be represented as multi-block or segmented copolymers having a random distribution of segments $(AB)_r$, wherein 'A' corresponds to the pre-polymer (A) segment A and 'B' corresponds to the pre-polymer (B) segment (for z=0). In $(AB)_r$, the A/B ratio (corresponding to x/y in formula (1)) may be unity or away from unity. The pre-polymers can be mixed in any desired amount and can be coupled by a multifunctional chain-extender, viz, a compound having at least two functional groups by which it can be used to chemically link the pre-polymers. In one embodiment, this is a difunctional chain-extender. In case z≠0, then the presentation of a random distribution of all the segments can be given by $(ABC)_r$, were three different pre-polymers (one being a segment derived from a water-soluble polymer such as PEG) are randomly distributed in all possible ratios.

The pre-polymers of which the a and b (and optionally c) segments are formed in $(AB)_r$ and $(ABC)_r$ are linked by the multifunctional chain-extender. This chain-extender is in one embodiment a diisocyanate chain-extender, but can also be a diacid or diol compound. In case the pre-polymers all contain hydroxyl end-groups and a diisocyanate chain-extender is used, the linking units will be urethane groups. In case (one of) the pre-polymers (is) are carboxylic acid terminated, the linking units are amide groups. Multi-block copolymers with structure $(AB)_r$ and $(ABC)_r$ can also be prepared by reaction of di-carboxylic acid terminated pre-polymers with a diol chain-extender or vice versa (diol terminated pre-polymer with diacid chain-extender) using a coupling agent such as DCC (dicyclohexyl carbodiimide) forming ester linkages.

As mentioned above, randomly segmented copolymers refer to copolymers that have a random distribution (i.e. not alternating) of the pore-polymer (A) segments and pre-polymer (B) segments.

The hydrolysable segment $R^1$—H—$R^1$ of formula (1) is obtained by reaction of pre-polymer (A).

Pre-polymer (A) may e.g. be prepared by ring-opening polymerisation. Thus, a pre-polymer (A) may be a hydrolysable copolymer prepared by ring-opening polymerisation initiated by a diol or diacid compound, in one embodiment having a random monomer distribution. The diol compound is in one embodiment an aliphatic diol or a low molecular weight polyether such as PEG. The polyether is part of the pre-polymer (A) by using it as an initiator and it can additionally be mixed with the pre-polymer (A), thus forming an additional hydrophilic segment $R^3$ in formula (1). Pre-polymer (A) may be a hydrolysable polyester, polyetherester, polycarbonate, polyestercarbonate, polyanhydride or copolymers thereof. For example, pre-polymer (A) comprises reaction products of ester forming monomers selected from diols, dicarboxylic acids and hydroxycarboxylic acids. Pre-polymer (A) may comprise reaction products of cyclic monomers and/or non-cyclic monomers. Exemplary cyclic monomers include glycolide, L-lactide, D-lactide, D,L-lactide, ε-caprolactone, δ-valerolactone, trimethylene carbonate, tetramethylene carbonate, 1,5-dioxepane-2-one, 1,4-dioxane-2-one (p-dioxanone) and/or cyclic anhydrides such as oxepane-2,7-dione. In one embodiment, ε-caprolactone is used.

To fulfil the requirement of a $T_g$ below 37° C., some of the above-mentioned monomers or combinations of monomers are more preferred than others. For example, pre-polymer (A) containing the monomers e-caprolactone is in one embodiment combined with any of the other mentioned cyclic co-monomers (glycolide, L-lactide, D-lactide, D,L-lactide, δ-valerolactone, trimethylenecarbonate, 1,4-dioxane-2-one and combinations thereof). This may by itself lower the $T_g$. Alternatively, the pre-polymer can be initiated with a PEG with sufficient molecular weight to lower the $T_g$ of the multi-block copolymer.

In case pre-polymer (A) contains poly(D,L-lactide), the L/D ratio of the lactide may be away from unity (other than 50/50). For instance, an L/D ratio between 85/15 and 15/85 gives a completely amorphous homopolymer. Furthermore, it is known that an excess of one isomer (L or D) over the other increases the $T_g$ of the poly(D,L-lactide). A minor amount of any other of the above-mentioned monomers that build the amorphous phase may also be present in the crystalline phase forming pre-polymer or block.

Furthermore, pre-polymer (A) can be based on (mixtures of) condensation (non-cyclic) type of monomers such as hydroxyacids (e.g. lactic acid, glycolic acid, hydroxybutyric acid), diacids (e.g. glutaric, adipic or succinic acid, sebacic acid) and diols such as ethylene glycol, diethylene glycol, 1,4-butanediol or 1,6-hexanediol, forming ester and/or anhydride hydrolysable moieties.

It is preferred that at least part of pre-polymer (A) is derived from a water-soluble polymer. The water-soluble polymer may comprise one or more selected from the group consisting of polyethers such as polyethylene glycol (PEG), polytetramethyleneoxide (PTMO) and polypropyleneglycol (PPG); polyvinylalcohol (PVA); polyvinylpyrrolidone (PVP); polyvinylcaprolactam; poly(hydroxyethylmethacrylate) (poly-(HEMA)); polyphosphazenes; polyorthoesters; polyorthoesteramides or copolymers of the previous polymers. In one embodiment, at least part of pre-polymer (A) is derived from PEG.

Some non-limiting examples of suitable pre-polymer (A) segments include poly(ε-caprolactone)-co-PEG-co-poly(ε-caprolactone), poly(D,L-lactide)-co-PEG-co-poly(D,L-lactide), poly(glycolide)-co-PEG-co-poly(glycolide), and polyp-dioxanone)-co-PEG-co-polyp-dioxanone).

In any addition, the pre-polymer (A) segment may, at each side of the water-soluble polymer, comprise any copolymer of the above-mentioned monomers. Some non-limiting examples of such pre-polymer (A) segments include [poly(ε-caprolactone-co-D,L-lactide)]-co-PEG-co-[poly(ε-caprolactone-co-D,L-lactide)], [poly(ε-caprolactone-co-glycolide)]-co-PEG-co-[poly(ε-caprolactone-co-glycolide)], [poly(ε-caprolactone-co-p-dioxanone)]-co-PEG-co-[poly(ε- caprolactone-cop-dioxanone)], [poly(D,L-lactide-co-gly-colide)]-co-PEG-co-[poly(D,L-lactide-co-glycolide)], [poly(D,L-lactide-co-p-dioxanone)]-co-PEG-co-[poly(D,L-lactide-co-p-dioxanone)], and [poly(glycolide-co-p-dioxanone)]-co-PEG-co-[poly(glycolide-co-p-dioxanone)].

Suitably, 30°i° or more by total weight of pre-polymer (A) is derived from a water-soluble polymer, such as 40% or more, 50% or more, 60% or more, or 70% or more. Suitably, 95% or less by total weight of pre-polymer (A) is derived from a water-soluble polymer, such as 90% or less, 85% or less.

Pre-polymer (A) can further comprise p-dioxanone. Such introduction of p-dioxanone monomers in the pre-polymer (A) segment can introduce additional crystallinity in the multi-block copolymers. The content of such p-dioxanone monomers in pre-polymer (A) may be 80% or less by weight of the pre-polymer (A), such as 60% or less, 50% or less, 40% or less, 30% or less, 20% or less, 10% or less, or 5% or less. The content of p-dioxanone monomers in pre-polymer (A) can be 0.1% or more, such as 1% or more, or 2% or more.

Pre-polymer (A) can have an $M_n$ of 500 g/mol or more, and in another embodiment 1000 g/mol or more, 1500 g/mol or more, or 2000 g/mol or more. The length of the pre-polymers must be chosen in such a way that they are as large as is necessary to obtain a good phase separated morphology and good mechanical and thermal properties of the resulting copolymer. Typically, pre-polymer (A) has an $M_n$ of 10 000 g/mol or less. The content of pre-polymer (A) in the copolymer is in one embodiment 5-95% based on total weight of the multi-block copolymer: in another embodiment, the content of pre-polymer (A) in the copolymer is 10-90%, 25-80% 40-70%, or 50-60%.

The segment $R^2$ of formula (1) may be obtained by reaction of pre-polymers (B) derived from poly(p-dioxanone). Optional further monomers present in pre-polymer (B) can be selected from L-lactide, D-lactide, hydroxybutyrate, glycolide and combinations thereof.

The pre-polymer (B) segment comprises polyp-dioxanone). Poly(p-dioxanone) can be synthesised by reacting p-dioxanone monomers in the presence of a suitably catalyst and a polymerisation initiator. Suitable polymerisation initiators are mentioned hereinabove.

The polymerisation reaction may be performed at a temperature of 10-120° C.; in another embodiment, the reaction may be performed at 50-100° C., 60-95° C., 70-90° C., or 75-85° C. The catalyst is a catalyst effective in promoting the polymerisation reaction and can suitably be selected from the group consisting of tin octoate based catalysts or tin titanate based catalysts. A preferred catalyst is stannous octoate, i.e. tin bis(2-ethylhexanoate). The monomer to catalyst molar ratio can be 20 000 or more, such as 21 000 or more. The monomer to catalyst molar ratio can be 35 000 or less, such as 34 000 or less. The reaction is in one embodiment conducted under nitrogen atmosphere.

The pre-polymer (B) segment comprises a X-Y-X triblock copolymer, wherein the block length of the poly(p-dioxanone) segment X expressed in terms of p-dioxanone monomer units is 7 or more. Pre-polymer (B) may have a number average molecular weight $M_n$ of 1300 g/mol or more, such as 1500 g/mol or more, 2000 g/mol or more, 2200 g/mol or more, or 2500 g/mol or more. The pre-polymer (B) may have a number average molecular weight $M_n$ of 7200 g/mol or less, such as 5000 g/mol or less, 4500 g/mol or less, 4000 g/mol or less, or 3200 g/mol or less.

Pre-polymer (B) can have a weight average molecular weight $M_w$ of 1800 g/mol or more, such as 2100 g/mol or more, 2600 g/mol or more, or 3000 g/mol or more. Pre-polymer (B) can have a weight average molecular weight $M_w$ of 10 080 g/mol or less, 7000 g/mol or less, such as 6300 g/mol or less, 5600 g/mol or less, or 4200 g/mol or less.

Suitably, 70% or more by total weight of the said pre-polymer (B) segment can be poly(p-dioxanone). In one embodiment, 80% or more by total weight of the said pre-polymer (B) segment can be poly(p-dioxanone). In another embodiment 85% or more, 90% or more, or 95% or more by total weight of the said pre-polymer (B) segment can be polyp-dioxanone). In one embodiment 80% or more by total weight of the X segment is polyp-dioxanone). In another embodiment, 85% or more, 90% or more, or 95% or more by total weight of the X segment is poly(p-dioxanone). In one embodiment, said X segment consists of polyp-dioxanone).

The content of pre-polymer (B) in the copolymer may be 10-90% based on total weight of the multi-block copolymer. The content of pre-polymer (B) in the copolymer can, for example, be 25-90%, 25-70%, or 30-50% based on total weight of the multi-block copolymer. Such contents generally result in the desired materials with good physical (e.g. swelling) and degradation properties at the temperature of application (viz, about 37° C. for medical applications).

The pre-polymers will in one embodiment be linear and random (co)polyesters, polyester-carbonates, polyetheresters, or polyanhydrides with reactive end-groups. These end-groups may be hydroxyl or carboxyl. It is preferred to have a dihydroxy terminated copolymer, but hydroxy-carboxyl or dicarboxyl terminated polymers can also be used. In case the polymer has to be linear, it can be prepared with a difunctional component (diol) as a starter, but in case a three or higher functional polyol is used, star shaped polyesters may be obtained. The diol in pre-polymer (A) can be an aliphatic diol or a low molecular weight polyether.

The pre-polymer synthesis by a ring-opening polymerisation is in one embodiment carried out in the presence of a catalyst. A suitable catalyst is $Sn(Oct)_2$ with M/I=5000-30 000 (M/I is the monomer to initiator ratio). It is also possible to carry out the synthesis without a catalyst.

The conditions for preparing the polyesters, polycarbonates and polyanhydrides are those known in the art.

The multi-block copolymer of the invention can suitably comprise 3-45% by total weight of the multi-block copolymer of water-soluble polymer (e.g. poly(ethylene glycol), such as 4-40% by total weight of the multi-block copolymer.

The multi-block copolymer of the invention can suitably comprise 30-70% by total weight of the multi-block copolymer of polyp-dioxanone), such as 35-65% by total weight of the multi-block copolymer, or 40-60%.

The copolymers of the invention are generally linear. However, it is also possible to prepare the copolymers in a branched form. These non-linear copolymers of the invention may be obtained by using a trifunctional (or higher functional) chain-extender, such as tri-isocyanate. Branched copolymers may show improved creep characteristics.

In an embodiment, the multi-block copolymer of the invention is a poly(ether ester) multi-block copolymer wherein the pre-polymer (A) segment comprises one or more selected from the group consisting of

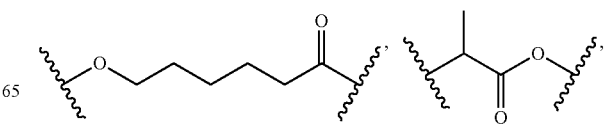

-continued

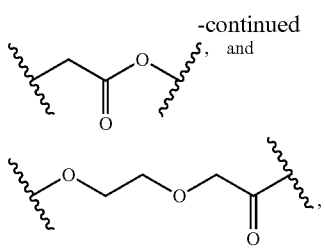

and wherein the pre-polymer (A) segment further comprises

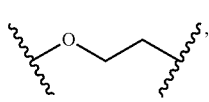 [SMILES: *CCO*]

and wherein the pre-polymer (B) segment comprises

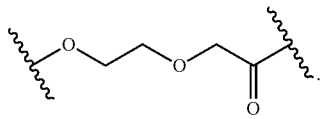 [SMILES: *OCCOCC(*)=O]

The pre-polymer (A) segment may, for example, be represented by

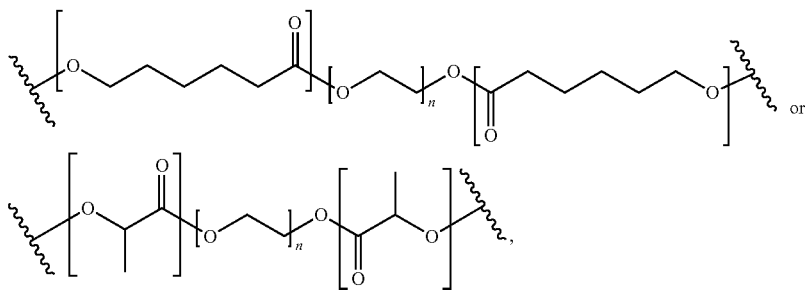

wherein n is 4-115, such as 13-70, or 20-46.

In an embodiment, the thermoplastic multi-block copolymer of the invention is represented by the formula $[(R^1R^2{}_nR^3)_q]_r[(R^4{}_pR^5R^6{}_p)]_s$, wherein $R^1$ and $R^3$ are independently selected from the group consisting of

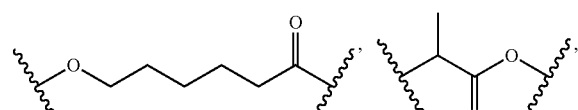

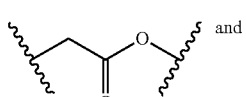

$R^2$ is

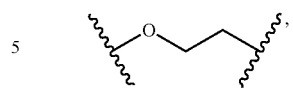

and
$R^4$ and $R^6$ are each

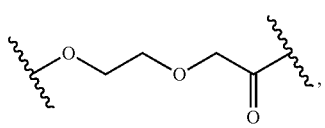 [SMILES: *OCCOCC(*)=O]

n, being the number of repeating $R^2$ moieties, is 4-120;
p, being the number of repeating $R^4$ and $R^6$ moieties is 7 or more;
q, being the molecular weight of the $(R^1R^2{}_nR^3)$ block is 400-10 000 g/mol;
r/s, being the ratio of pre-polymer (A) segment over pre-polymer (B) segment is 0.1-2.5.

In this denotation, n is the number of repeating $R^2$ moieties, q is the (number average) molecular weight of the $(R^1R^2{}_nR^3)$ block, r is the weight percentage of the $(R^1R^2{}_nR^3)_q$ block, p is the number of repeating $R^4$ and $R^6$ moieties, and s is the weight percentage of the $(R^4{}_pR^5R^6{}_p)$ block.

Suitably, n can be 4-120, such as 13-70, more preferably 20-46.

Suitably, p can be 7 or more, such as 8 or more, 9 or more, 10 or more, 11 or more 12 or more, or 14 or more. The upper limit of p is less critical, but may for example be 35 or less, such as 30 or less, 25 or less, 20 or less, 15 or less, or 14 or less.

Suitably, q can be 400-10 000 g/mol, such as 600-8000 g/mol, 1000-6000 g/mol, 1200-5000 g/mol, 1400-4000 g/mol, 1600-3000 g/mol, or 1800-2200 g/mol.

Suitably, r can be 20-80, such as 30-75, 40-70, or 50-65.
Suitably, s can be can be 20-80, such as 25-70, 30-60, or 35-50.

The number average molecular weight of the $(R^4{}_pR^5R^6{}_p)$ block (corresponding to the pre-polymer (B) segment) can be 1300-7200 g/mol, preferably 1300-5000 g/mol, more preferably 1500-4500 g/mol, most preferably 2000-4000 g/mol, such as 2200-3200 g/mol.

The weight average molecular weight of the $(R^4{}_pR^5R^6{}_p)$ block (corresponding to the pre-polymer (B) segment) can be 1800-10 080 g/mol, 1800-7000 g/mol, such as 2100-6300 g/mol, 2600-5600 g/mol, or 3000-4200 g/mol.

In a further aspect the invention is directed to a process for preparing the phase separated, thermoplastic multi-block copolymers of the invention, comprising a chain-extension reaction of pre-polymer (A) and pre-polymer (B) in the presence of a multifunctional chain-extender, thereby obtaining a randomly segmented multi-block copolymer.

Segmented multi-block copolymers with structure $(AB)_r$ and $(ABC)_r$ can be made by chain-extending a mixture of the pre-polymers, containing the hard and the soft segments forming monomers of segments $R^1$, H and $R^2$, and optionally $R^3$, in the desired ratio with an equivalent amount of a multifunctional chain-extender, in one embodiment an aliphatic molecule, such as 1,4-butanediisocyanate (BDI) or another diisocyanate. The segmented copolymers of structures $(AB)_r$ or $(ABC)_r$ are in one embodiment made in solution. Suitably, the pre-polymer(s) are dissolved in an inert organic solvent and the chain-extender is added pure or in solution. The polymerisation temperature can be the same or even lower than the highest phase transition temperature of the pre-polymers. Coupling reactions with dicyclohexyl carbodiimide (DCC) are in one embodiment carried out in solution. Two (or three) pre-polymers that are all diol or diacid terminated may be mixed in solution with a diacid or diol terminated chain-extender, respectively, after which DCC is added.

Polymerisation takes place for a time long enough to obtain an intrinsic viscosity of the copolymer of 0.1 dl/g or higher (measured at 25° C. in chloroform). The low polymerisation temperature and short polymerisation time will prevent transesterification so that the phase separated morphology is obtained and the monomer distribution is the same as in the pre-polymers that build the copolymer. On the contrary, high molecular weight random copolymers have to be prepared using longer reaction times to achieve complete incorporation of pre-polymers. Longer reaction times may lead to transesterification reactions and to a more random (i.e. less blocky) monomer distribution.

The materials obtained by chain-extending in the bulk can also be produced in situ in an extruder.

If the chain-extender is a difunctional, aliphatic molecule and the pre-polymers are linear, a linear copolymer is made. If one of the reactants (either the chain-extender or at least one of the pre-polymers) or both have more than two functional groups, branched structures may be obtained at sufficiently low conversion. The chain-extender can be a difunctional aliphatic chain-extender, in one embodiment a diisocyanate such as 1,4-butanediisocyanate.

The combination of crystalline and amorphous phase forming pre-polymers or monomers is chosen in such a way to obtain a phase separated segmented or block co-polyester or polyester-carbonate with the desirable degradation, swelling, physical and thermal properties. Typically, the intrinsic viscosity is larger than 0.1 dl/g and less than 10 dl/g (measured at 25° C. in chloroform), in one embodiment between 0.1-2 dl/g, and in another embodiment between 0.2-1 dl/g.

In a further aspect, the invention is directed to a process for preparing a biodegradable, phase separated, thermoplastic multi-block copolymer comprising:

i) performing a chain extension reaction of pre-polymer (A) and pre-polymer (B) in the presence of a multifunctional chain-extender, wherein pre-polymer (A) and (B) are both diol or diacid terminated and the chain-extender is dicarboxylic acid, diisocyanate, or diol terminated; or ii) performing a chain extension reaction using a coupling agent, wherein pre-polymer (A) and (B) are both diol or diacid terminated and the coupling agent is in one embodiment dicyclohexyl carbodiimide, wherein the pre-polymer (B) segment comprises a X-Y-X tri-block copolymer, wherein Y is a polymerisation initiator, and X is a poly(p-dioxanone) segment with a block length expressed in p-dioxanone monomer units of 7 or more.

The multi-block segmented copolymers can be formed into formulations of various shape and dimensions using any known technique such as, for example, solvent extraction/evaporation-based emulsification processes, extrusion, moulding, solvent casting, spray-drying, spray-freeze drying, electrospinning, or freeze drying. The latter technique is used to form porous materials. Porosity can be tuned by addition of co-solvents, non-solvents and/or leachables. Copolymers can be processed (either solid or porous) into microspheres, microparticles, nanospheres, rods, films, sheets, sprays, tubes, membranes, meshes, fibres, plugs, coatings and other articles. Products can be either solid, hollow or (micro)porous. A wide range of biomedical implants can be manufactured for applications in for example wound care, skin recovery, nerve regeneration, vascular prostheses, drug delivery, meniscus reconstruction, tissue engineering, coating of surgical devices, ligament and tendon regeneration, dental and orthopaedic repair. The copolymers can be used alone or can be blended and/or co-extruded with other absorbable or non-absorbable polymers.

Furthermore, they can be used in pharmaceutical applications, e.g. for drug delivery, e.g. in the form of microspheres, nanoparticles, solid implants, gels, coatings, films, sheets, sprays, tubes, membranes, meshes, fibres, plugs, and other configurations.

As will be illustrated in the examples below, the materials of the invention have improved properties, including thermal, mechanical, processing compared to copolymers described in the prior art.

In yet a further aspect, the invention is directed to a composition for the delivery of at least one biologically active compound (e.g. a biologically active small molecule, protein or peptide) to a host, comprising the at least one biologically active compound encapsulated in a matrix, wherein said matrix comprises at least one phase separated, thermoplastic multi-block copolymer as defined herein.

The biodegradable multi-block copolymers of the invention are particularly suitable as delivery vehicle for a polypeptide, allowing for the controlled release of the polypeptide from the matrix into its environment, e.g. in the body of a subject.

The multi-block copolymers of the invention have many options for tuning the release properties of the delivery composition for the specific application. The release rate of the biologically active compound may for example be increased by:

increasing the molecular weight of the water-soluble polymer in pre-polymer (A) at constant molecular weight of pre-polymer (A);

increasing the molar ratio between pre-polymer (A) and pre-polymer (B);

increasing the content of a monomer that gives a faster degrading polymer in pre-polymer (A), e.g. by replacing ε-caprolactone by D,L-lactide or glycolide or by replacing D,L-lactide with glycolide;

decreasing the molecular weight of pre-polymer (B) at a constant molar ratio between pre-polymer (A) and pre-polymer (B) (this increases the pre-polymer (A)

weight percentage and also decreases the $T_m$ of pre-polymer (B) and the total amount of crystalline phase present);

decreasing the molecular weight of pre-polymer (A) at a constant molecular weight of the water-soluble polymer and molar ratio between pre-polymer (A) and pre-polymer (B); and/or the use of an additional, third segment derived from a water-soluble polymer, whereby the content of the water-soluble polymer is increased.

The release rate may be decreased by the opposite changes as mentioned above, as well as by increasing the $T_m$ of segment B;

the use of an additional, third segment derived from a water-soluble polymer diol, whereby a diisocyanate is used as chain-extender and the water-soluble polymer content is held constant or is decreased. The water-soluble polymer in the third segment is built in the multi-block copolymer with a slowly degrading urethane bond, compared to a faster degrading ester bond of the water-soluble polymer in pre-polymer (A).

Biologically active compounds which may be contained in the multi-block copolymer matrix, such as a [poly(D,L-lactide)-co-PEG-co-poly(D,L-lactide)]-b-[poly(p-dioxanone)], [poly(glycolide)-coo-PEG-co-poly(glycolide)]-b-[poly(p-dioxanone)], or [poly(ε-caprolactone)-co-PEG-co-poly(ε-caprolactone)]-b-[poly(p-dioxanone)], or [poly(ε-caprolactone-co-D,L-lactide)-co-PEG-co-poly(ε-caprolactone-co-D,L-lactide)]-b-[poly(p-dioxanone)] matrix, include but are not limited to non-peptide, non-protein small sized drugs having a molecular weight which in general is 1000 Da or less and biologically active polypeptides.

When a small-sized drug is contained in the multi-block copolymer matrix (such as a [poly(D,L-lactide)-co-PEG-co-poly(D,L-lactide)]-b-[poly(p-dioxanone)], [poly(glycolide)-co-PEG-co-poly(glycolide)]-b-[poly(p-dioxanone)], [poly(ε-caprolactone)-co-PEG-co-poly(ε-caprolactone)]-b-[poly(p-dioxanone)], or [poly(ε-caprolactone-co-D,L-lactide)-co-PEG-co-poly(ε-caprolactone-co-D,L-lactide)]-b-[poly(p-dioxanone)] matrix), the PEG component of the copolymer in one embodiment has a molecular weight of 200-1500 g/mol, and in another embodiment 600-1000 g/mol, and is present in the copolymer in an amount of 5-20% by total weight of the copolymer, or 5-10% by total weight of the copolymer. The at least one small-sized drug molecule may be present in the matrix in an amount of 0.1-80% by total combined weight of the matrix and the at least one small-sized drug molecule, in one embodiment 1.0-40%, and in another embodiment 5-20%. If it is desired to increase the hydrophilicity of the multi-block copolymer, and thereby increase the degradation rate of the copolymer and the release rate of the incorporated biologically active compound, the copolymer may be modified by replacing partially or completely the D,L-lactide of the hydrophilic pre-polymer (A) segment by glycolide and/or by using a PEG component with a higher molecular weight or by increasing the weight fraction of PEG component in the pre-polymer (A) segment. If it is desired to decrease the hydrophilicity of the polymer, and thereby decrease the degradation rate of the copolymer, and the release rate of the incorporated biologically active compound, the copolymer may be modified by replacing partially or completely the D,L-lactide of the hydrophilic pre-polymer (A) segment by e-caprolactone and/or by using a PEG component with a lower molecular weight or by decreasing the weight fraction of PEG component in the pre-polymer (A) segment.

A polypeptide consists of amino acids linked by peptide bonds. Short polypeptides are also referred to as peptides, whereas longer polypeptides are typically referred to as proteins. One convention is that those polypeptide chains that are short enough to be made synthetically from the constituent amino acids are called peptides rather than proteins. However, with the advent of better synthetic techniques, polypeptides as long as hundreds of amino acids can be made, including full proteins like ubiquitin. Another convention places an informal dividing line at approximately 50 amino acids in length. This definition is somewhat arbitrary. Long polypeptides, such as the amyloid beta peptide linked to Alzheimer's disease, can be considered proteins; and small proteins, such as insulin, can be considered peptides. At any rate, the skilled person will appreciate that essentially any type of polypeptide can be encapsulated and subsequently released from a copolymer matrix.

In one embodiment, a composition of the invention comprises a biologically active peptide or biologically active protein.

The size of the polypeptide(s) can vary. In one embodiment, the polypeptide has a molecular weight of 10 000 Da or less. Polypeptides of such size are particularly suitable to be encapsulated in the matrix of a copolymer comprising PEG as a segment of pre-polymer (A) and/or as an additional pre-polymer, said PEG having a number average molecular weight of 400-3000 g/mol, or in another embodiment 600-1500 g/mol. Alternatively, or in addition, said PEG can be present in an amount of 5-60% by total weight of the copolymer, or in another embodiment 5-40%.

In another embodiment, said polypeptide is a biologically active protein having a molecular weight of 10 000 Da or more. These larger polypeptides are in one embodiment encapsulated in the matrix of a copolymer which contains PEG, as a segment of pre-polymer (A) and/or as an additional pre-polymer, and wherein said PEG has a number average molecular weight of 600-5000 g/mol, or in another embodiment 1000-3000 g/mol. Alternatively, or in addition, said PEG can be present in an amount of 5-70% by total weight of the copolymer, or in another embodiment 10-50%.

A composition of the invention can have any desirable appearance or shape. In one embodiment, multi-block copolymers of the current invention are processed in the form of microspheres, microparticles, sprays, an implant, a coating, a gel, a film, foil, sheet, membrane or rod.

One specific aspect relates to a composition in the form of microspheres. In general microspheres are fine spherical particles having a diameter of less than 1000 μm, and containing a biologically active compound. The microsphere may be a homogeneous or monolithic microsphere in which the biologically active compound is dissolved or dispersed throughout the polymer matrix. It is also possible that the microsphere is of a reservoir type in which the biologically active compound is surrounded by a polymer in the mononuclear or polynuclear state. When the biologically active compound is a small sized water-soluble drug, the drug may first be dispersed in a hydrophobic or lipophilic excipient, which combination then is dispersed in the form of particles, droplets, or microsuspensions in the polymer matrix. Microspheres can then be formed from the emulsion.

The microspheres may be prepared by techniques known to those skilled in the art, including but not limited to coacervation, solvent extraction/evaporation, spray drying or spray-freeze drying techniques.

In one embodiment, the microspheres are prepared by a solvent extraction/evaporation technique which comprises dissolving the multi-block copolymer in an organic solvent such as dichloromethane, and emulsification of the multi-block copolymer solution in an aqueous phase containing an emulsifying agent, such as polyvinyl alcohol (as described among others by Okada, *Adv. Drug Del. Rev.* 1997, 28(1), 43-70).

The characteristics, such as particle size, porosity and drug loading of the so-formed microspheres depend on the process parameters, such as viscosity or concentration of the aqueous polyvinyl alcohol phase, concentration of the multi-block copolymer solution, ratio of dichloromethane to aqueous solution of active, ratio of primary emulsion to polyvinyl alcohol phase and the stirring rate.

When the microspheres are formed by a spray-drying process, a low concentration of multi-block copolymer from 0.5-5% by total weight of the solution, in one embodiment about 2%, in the organic solvent, such as dichloromethane, is employed. Spray-drying results in general in the formation of porous, irregularly shaped particles.

As the microspheres are being formed, a biologically active compound is encapsulated in the microspheres or microparticles. In general, when the solvent extraction/evaporation technique is employed to encapsulate lipophilic compounds, the compound is first dissolved in the solution of the multi-block copolymer in an organic solvent such as dichloromethane or ethyl acetate. The organic solution is then subsequently emulsified in an aqueous polyvinyl alcohol solution, which yields an oil-in-water (O/W) emulsion. The organic solvent is then extracted into the aqueous phase and evaporated to solidify the microspheres.

In general, when the solvent evaporation technique is employed to encapsulate water-soluble compound, an aqueous solution of the compound is first emulsified in a solution of the multi-block copolymer in an organic solvent such as dichloromethane. This primary emulsion is then subsequently emulsified in an aqueous polyvinyl alcohol solution, which yields a water-in-oil-in-water (W/O/W) emulsion. The organic solvent, such as dichloromethane or ethyl acetate, is then extracted similarly to the O/W process route to solidify the microspheres. Alternatively, water-soluble agents may be dispersed directly in a solution of the multi-block copolymer in an organic solvent. The obtained dispersion is then subsequently emulsified in an aqueous solution comprising a surfactant such as polyvinyl alcohol, which yields a solid-in-oil-in-water (S/O/W) emulsion. The organic solvent is then extracted similarly to the O/W process route to solidify the microspheres.

When W/O/W and S/O/W emulsification routes are used to encapsulate water-soluble compound, it may be challenging to obtain microspheres with sufficient encapsulation efficiency. Due to the water-soluble character of the compound, part of the compound may be lost to the aqueous extraction medium such as aqueous polyvinyl alcohol solution. A viscosifier, such as gelatine, may be used in the internal water phase, to decrease diffusion of the compound in the internal water phase to the external water phase. Also, additives may be added to the external water phase to decrease the solubility of the compound in the external water phase. For this purpose, salts may be used or the pH may be adjusted.

Water-in-oil-in-oil (W/O/O) or solid-in-oil-in-oil (S/O/O) emulsification routes provide an interesting alternative to obtain microspheres with sufficient encapsulation efficiency. In the W/O/O process the biologically active compound is, similar to a W/O/W process, dissolved in an aqueous solution and emulsified with a solution of the polymer in an organic solvent, such as typically dichloromethane or ethyl acetate. Subsequently, a polymer precipitant, such as silicon oil, is then slowly added under stirring to form embryonic microparticles, which are then poured into heptane or hexane to extract the silicone oil and organic solvent and solidify the microspheres. The microparticles may be collected by vacuum filtration, rinsed with additional solvent and dried under vacuum. In the S/O/O emulsification route the biologically active compound is, similar to a S/O/W process, dispersed as a solid powder in a solution of the polymer in an organic solvent, such as dichloromethane or ethyl acetate. Subsequently, a polymer precipitant, such as silicon oil, is then slowly added under stirring to form embryonic microparticles, which are then poured into heptane or hexane to extract the silicone oil and dichloromethane and solidify the microspheres.

Stabilising agents may be added to the aqueous solution of protein to prevent loss of protein activity during processing into microspheres. Examples of such stabilising agents are polyvinyl alcohol, Tween®/polysorbatum, human serum albumin, gelatine and carbohydrates, such as trehalose, inulin and sucrose.

When the spray-drying technique is employed, an aqueous solution of the compound is emulsified in a solution of the copolymer in an organic solvent such as methylene chloride, as hereinabove described. The water-in-oil emulsion is then spray-dried using a spray dryer.

In further embodiments, the composition of the invention is in the form of a coating, an injectable gel, an implant (such as an injectable implant) or a coated implant. The composition in the form of a coating may be applied as a drug-eluting coating e.g. on a medical implant, such as a vascular or urinary stent, an orthopaedic prosthesis or an ocular implant.

Biologically active compounds may be formulated into injectable solid implants via extrusion. Typically, the compound and multi-block copolymer powders are physically mixed where after the resulting powder blend is introduced to the extruder, heated and processed to yield formulations of the desired shape and dimensions, such as a small diameter cylindrical rod. Instead of physical mixing of the compound and multi-block copolymer powders, the compound and polymer may be co-dissolved in a suitable solvent or a dispersion of compound in a solution of polymer in a suitable solvent may be prepared, followed by freeze-drying and extrusion of the freeze-dried powder. The latter generally improves the blend homogeneity and the content uniformity of the implants.

In yet another aspect the invention is directed to a method of delivering a biologically active compound to a subject in need thereof comprising administering an effective dose of a composition as defined herein to said subject.

The subject is typically a mammal, preferably a human. However, veterinary use of the invention is also encompassed. The method can have a therapeutic, prophylactic, and/or cosmetic purpose. Any suitable mode of administration can be selected, depending on the circumstances. For example, administering may comprise the parenteral, oral, intra-arterial, intra-articular, intra-venal, intra-ocular, epidural, intra-thecal, intra-muscular, intra-peritoneal, intravenous, intra-vaginal, rectal, topical or subcutaneous administration of the composition. In one embodiment, the invention provides a method for delivering a biologically active polypeptide of interest to a subject in need thereof, comprising administering an effective dose of a composition according to the invention to said subject, wherein the composition is in the form of microspheres, an injectable implant or an in, situ forming gel and wherein the composition is administered intraocularly, intra-arterially, intramuscularly or subcutaneously.

For topical administration, the microspheres may be contained in a gel, cream, or ointment, and may, if desired, be covered by a barrier. Thus, the microspheres may contain one or more biologically active compounds employed in the treatment of skin diseases, such as psoriasis, eczema, seborrhoea, and dermatitis.

In another embodiment, the microspheres may be contained in a gel such as a hyaluronic acid gel or a macromolecular polysaccharide gel. Such an embodiment is applicable particularly to parenteral applications, such as during and after surgery.

When administered via injection, the microspheres may be contained in a pharmaceutical carrier such as water, saline solution (for example, 0.9%), or a solution containing a surfactant in an amount of from 0.1-0.5% w/v. Examples of surfactants which may be employed include, but are not limited to, Tween 80 surfactant. The pharmaceutical carrier may further contain a viscosifier, such as sodium carboxymethylcellulose.

Such microspheres, when administered in combination with an acceptable pharmaceutical carrier, may be employed in the treatment of a variety of diseases or disorders, depending upon the biologically active compound that is encapsulated.

In one aspect, provided herein are injectable delivery systems comprising a poly(ether ester) multi-block copolymer (PEE-MBCP) provided herein.

The PEE-MBCP can be in the form of an implant. Such implant may be a microsphere, a rod, a film, a PEE-MBCP depot, or a plurality thereof. The PEE-MBCP may in the form of a plurality of polymeric microspheres that are each not less than 20 µm in diameter, wherein the polymeric microspheres comprise the PEE-MBCP as described herein. The polymeric microspheres can be from 20 µm to 80 µm in diameter, such as from 30 µm to 70 µm in diameter. The polymeric microspheres may be monodisperse with a coefficient of variation of about 25%. The injectable delivery systems may further comprise a therapeutic agent, or a pharmaceutically acceptable salt thereof. The therapeutic agent may be a small chemical, a protein, an antibody, a peptide or an oligonucleotide, or a combination thereof. Additionally, the injectable delivery systems can further comprise a pharmaceutically acceptable excipient. An example of an injectable delivery system comprises a PEE-MBCP composed of a poly(ε-caprolactone)-co-PEG1000-co-poly(ε-caprolactone) pre-polymer (A) block in combination with a poly(p-dioxanone) pre-polymer (B) block with a molecular weight of approximately 2500 g/mol, in a block ratio of 60/40 wt. % (also abbreviated as 60CP10C20-D25), which may optionally comprise a small chemical, a protein, an antibody, a peptide or an oligonucleotide, or a combination thereof as active ingredient.

The invention has been described by reference to various embodiments, compositions and methods. The skilled person understands that features of various embodiments, compositions and methods can be combined with each other.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

For the purpose of clarity and a concise description features are described herein as part of the same or separate embodiments, however, it will be appreciated that the scope of the invention may include embodiments having combinations of all or some of the features described.

EXAMPLES

The invention will now be further illustrated by the following non-limiting examples.

In the following examples various biodegradable semi-crystalline, phase separated multi-block copolymers were synthesised and evaluated for their processing, drug release characteristics and erosion characteristics. The polymers were composed of a crystalline p-dioxanone-based hard pre-polymer (B) segment with a melting point ($T_m$) and a hydrophilic poly(ethylene glycol) (PEG)-based pre-polymer (A) segment having a glass transition temperature ($T_g$) that was below 37° C. under physiological conditions. In the following examples PEG is denoted with its molecular weight (MW). For example, PEG1000 refers to PEG with $M_w$ 1000 g/mol.

Example 1

PLGA polymers are most often used for sustained release of drugs and have been clinically proven to be safe in the body. Even though PLGA polymers are fairly versatile, and their physiochemical properties can be tuned to accommodate different drug delivery needs, their suitability has been shown to be limited in protein delivery. Protein stability remains a major obstacle in delivering proteins with PLGA due to (1) the hydrophobic character of the polymers, (2) the formation of acidic degradation products and the accumulation of acidic degradation products in the polymer matrix leading to an in situ pH drop due to which the any encapsulated proteins may degrade and lose their biological activity. Proteins have also been shown to be (3) chemically modified through deamination or acylation within the PLGA matrix. Consequently, delivery systems made with PLGA are associated with all the issues as mentioned above including (4) protein aggregation and (5) undesirable release kinetics.

Biodegradable phase separated segmented multi-block copolymers (SynBiosys, InnoCore Technologies B.V, Groningen, The Netherlands) as disclosed in WO-A-2012/005594 and WO-A-2013/015685 have been developed to deliver peptides and proteins structurally intact and biologically active over extended periods of time up to three to six months. SynBiosys multi-block co-polymers are typically composed of two different blocks in which commonly used monomers including D,L-lactide, glycolide, c-caprolactone and polyethylene glycol (PEG) are copolymerized into low molecular weight polymers (a pre-polymer), which are linked together with a diisocyanate, typically 1,4-butanediisocyanate. By using two chemically and physically distinct pre-polymer blocks, such as a hydrophilic amorphous and a hydrophobic crystalline domain, a phase separated segmented multi-block copolymer is obtained that provides mechanisms for long term release of drugs including peptides and proteins. The hydrophilic amorphous blocks typically contain a high content of polyethyleneglycol (PEG) which leads to swelling of the multi-block copolymer under aqueous conditions. The hydrophobic crystalline blocks act as physical crosslinks. Hydrophilic phase separated segmented multi-block copolymers containing a hydrophobic poly(ε-caprolactone)-based crystalline block, as disclosed in WO-A-2012/005594, allowed long term sustained release of peptides and proteins when processed into implants by hot melt extrusion (Stankovic et al., Eur. J. Pharm. Sci. 2013, 49(4), 578-587). Hydrophilic phase separated segmented multi-block copolymers containing a hydrophobic poly(L-lactide)-based crystalline block, as disclosed in WO-A-2013/015685, were previously shown to have highly beneficial attributes in regard to protein delivery. Especially multi-block copolymers composed of a poly(ε-Caprolactone)-PEG-poly(ε-Caprolactone)-based hydrophilic block in combination with a poly(L-lactide)-based crystalline block (PCL multi-block copolymers) were found to exhibit promising characteristics allowing long term sustained release of structurally intact biologics when formulated into microparticles (Teekamp et al., *Int. J. Pharm.* 2017, 534(1-2), 229-236; Teekamp et al., *J. Control Release* 2018, 269, 258-265: Scheiner et al., *ACS Omega* 2019, 4(7), 11481-11492).

PCL multi-block copolymers composed of a crystalline poly(L-lactide) block with a molecular weight ($M_n$) of 4000 g/mol (abbreviated as LL40) in combination with a hydrophilic poly(ε-caprolactone)-PEG1000-poly(ε-caprolactone) block with $M_n$ of 2000 g/mol (abbreviated as CP10C20) in block ratios varying from 20/80 (20CP10C20-LL40) to 50/50 (50CP10C20-LL40) and PCL multi-block copolymer composed of LL40 in combination with a hydrophilic poly (ε-caprolactone)-PEG3000-poly(ε-caprolactone) block with $M_n$ of 4000 g/mol (abbreviated as CP30C40) in a 30/70 (30CP30C40-LL40) or 50/50 (50CP30C40-LL40) weight ratio were found suitable for sustained release delivery of biologics of different molecular size such as goserelin, lysozyme, bovine serum albumin, insulin-like growth factor-1, hepatocyte growth factor and vascular endothelial growth factor.

Figure 1:
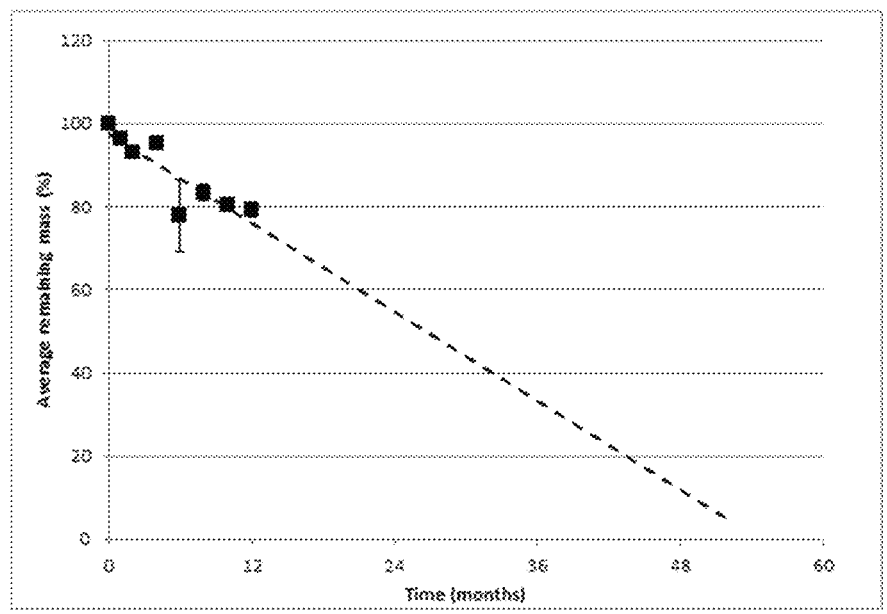
FIG. 1 In vitro erosion of 50CP10C20-LL40: experimental data up to 12 months and extrapolation of the experimental data up to complete erosion.

Unfortunately, 50CP10C20-LL40-based microspheres were found to degrade very slowly. Based on extrapolation of experimental data, the in vitro erosion time of the 50CP10C20-LL40 microspheres is projected to be 3-4 years (FIG. 1) and at least 14-16 months in vivo. The slow erosion of PCL multi-block copolymers was confirmed for other PCL multi-block copolymers such as 20CP10C20-LL40 and 30CP30C40-LL40 and attributed to slow hydrolysis of the crystalline poly(L-lactide) block.

A redesign of SynBiosys PCL multi-block copolymers was conducted in an attempt to reduce the erosion time of the polymer, avoid polymer accumulation upon repeated administration and improve the long term local tolerability. To increase its erosion rate, both the CP10C20 amorphous block and the crystalline LL40 block were altered. The crystalline LL40 block was altered by 1) partial replacement of L-lactide by D-lactide (L-MBCP concept), 2) use of more hydrophilic initiators for the synthesis of the crystalline L-lactide block (I-MBCP concept), 3) use of short stereo-complexed crystalline blocks composed of L-lactide and D-lactide (SC-MBCP concept); and 4) complete replacement of L-lactide by dioxanone (D-MBCP concept). The amorphous CP10C20 block was altered by changing the weight fractions and molecular weight of PEG, the length of the poly(ε-caprolactone) chains and by partial replacement of e-caprolactone by DL-lactide. Finally the ratio between the amorphous and crystalline block (block ratio) was altered.

L-MBCP Polymers

The various L-MBCP-based polymers that were synthesised are listed in Table 1. The table represents L-MBCP polymers that were prepared by chain-extending crystalline lactide-based crystalline blocks with D-lactide/L-lactide ratios of 0/100 (PCL05), 1/99, 4/96 and 7/93 mol/mol with amorphous CP10C20 or poly(DL-lactide-co-ε-caprolactone)-PEG 1000-poly(DL-lactide-coε-caprolactone) pre-polymers (LCP10LC20 with DL-lactide/ε-caprolactone ratios (L/C ratio) of 0/100, 5/95 and 15/85 mol/mol.

TABLE 1

Overview of L-MBCP polymers.

| | | Amorphous block | | Crystalline block | | | |
|---|---|---|---|---|---|---|---|
| RCP | Type | L/C ratio | PEG MW | MW | Type | DL/LL ratio | Block ratio | IV (dl/g) |
| 1446 | CP10C20 | 0/100 | 1000 | 2000 | LL40 | 0/100 | 50/50 | 0.85 |
| 1515 | CP10C20 | 0/100 | 1000 | 2000 | [DL/LL]40 | 4/96 | 50/50 | 0.98 |
| 1518 | CP10C20 | 0/100 | 1000 | 2000 | [DL/LL]40 | 1/99 | 50/50 | 1.00 |
| 1519 | CP10C20 | 0/100 | 1000 | 2000 | [DL/LL]40 | 7/93 | 50/50 | 1.12 |
| 1561 | CP10C20 | 0/100 | 1000 | 2000 | [DL/LL]40 | 7/93 | 30/70 | 0.87 |
| 1530 | LCP10LC20 | 5/95 | 1000 | 2000 | LL40 | 0/100 | 50/50 | 0.78 |
| 1532 | LCP10LC20 | 15/85 | 1000 | 2000 | LL40 | 0/100 | 50/50 | 0.73 |
| 1541 | LCP10LC20 | 5/95 | 1000 | 2000 | [DL/LL]40 | 4/96 | 50/50 | 0.96 |
| 1542 | LCP10LC20 | 15/85 | 1000 | 2000 | [DL/LL]40 | 4/96 | 50/50 | 0.90 |
| 1543 | LCP10LC20 | 15/85 | 1000 | 2000 | [DL/LL]40 | 7/93 | 50/50 | 0.85 |
| 1550 | LCP10LC20 | 5/95 | 1000 | 2000 | [DL/LL]40 | 4/96 | 30/70 | 0.88 |
| 1554 | LCP10LC20 | 15/85 | 1000 | 2000 | [DL/LL]40 | 7/93 | 30/70 | 0.92 |
| 1551 | LCP10LC20 | 15/85 | 1000 | 2000 | [DL/LL]40 | 4/96 | 30/70 | 0.91 |
| 1553 | LCP10LC20 | 5/95 | 1000 | 2000 | [DL/LL]40 | 7/93 | 30/70 | 0.81 |

I-MBCP Polymers

To prepare more hydrophilic L-lactide-based crystalline blocks, diethylene glycol (DEG) and triethyleneglycol (TEG) were used as initiator as an alternative for 1,4-butanediol. DEG and TEG initiated LL40 pre-polymer blocks were combined with either CP10C20 or LCP10LC20. Table 2 lists the DEG and TEG-based I-MBCP polymers.

TABLE 2

Overview of I-MBCP polymers.

| RCP | Type | Block 1 L/C ratio | Block 1 PEG MW | MW | Type | Initiator | Block ratio | IV (dl/g) |
|---|---|---|---|---|---|---|---|---|
| 1516 | CP10C20 | 0/100 | 1000 | 2000 | LL40 | DEG | 50/50 | 0.60 |
| 1517 | CP10C20 | 0/100 | 1000 | 2000 | LL40 | TEG | 50/50 | 0.73 |
| 1548 | LCP10LC20 | 15/85 | 1000 | 2000 | LL40 | TEG | 50/50 | 0.76 |
| 1564 | CP10C20 | 0/100 | 1000 | 2000 | LL40 | TEG | 40/60 | 0.87 |

D-MBCP Polymers

As an alternative to L-lactide-based crystalline blocks, poly(p-dioxanone) was evaluated. Poly(p-dioxanone) is a crystalline polyester but more hydrophilic than poly(L-lactide). Low molecular weight polydioxane-based pre-polymers were synthesised and chain-extended with CP10C20 and with alternative caprolactone-PEG-based pre-polymers with varying PEG molecular weight and poly(ε-caprolactone) chain lengths.

TABLE 3

Overview D-MBCP polymers.

| RCP | Type | Block 1 L/C ratio | Block 1 PEG MW | MW | Block 2 Type | Initiator | Block ratio | IV (dl/g) |
|---|---|---|---|---|---|---|---|---|
| 1502 | CP10C20 | 0/100 | 1000 | 2000 | Poly(p-dioxanone) | BDO | 57/43 | 1.43 |
| 1524 | CP30C40 | 0/100 | 3000 | 4000 | Poly(p-dioxanone) | BDO | 50/50 | 1.20 |
| 1556 | CP15C20 | 0/100 | 1500 | 2000 | Poly(p-dioxanone) | BDO | 50/50 | 0.95 |
| 1557 | CP30C40 | 0/100 | 3000 | 4000 | Poly(p-dioxanone) | BDO | 20/80 | 0.80 |
| 15102 | CP10C16.7 | 0/100 | 1000 | 1670 | Poly(p-dioxanone) | BDO | 60/40 | 0.79 |
| 1567 | CP15C20 | 0/100 | 1500 | 2000 | Poly(p-dioxanone) | BDO | 35/65 | 0.63 |
| 15106 | CP10C12.5 | 0/100 | 1000 | 1250 | Poly(p-dioxanone) | BDO | 40/60 | 0.61 |
| 15102 | CP10C16.7 | 0/100 | 1000 | 1670 | Poly(p-dioxanone) | BDO | 60/40 | 0.79 |

SC-MBCP Polymers

SC-MBCP polymers were obtained by chain extending amorphous pre-polymers with 50/50 wt. % mixtures of low molecular weight D-lactide pre-polymers (DL15, DL20) and L-lactide pre-polymers (LL15, LL20). D-Lactide blocks and L-lactide blocks will form highly crystalline blocks via stereo-complexation. DL15/LL15 or DL20/LL20 pre-polymer mixtures were combined with CP10C20, LCP10LC20 as well as with lower molecular weight amorphous pre-polymers composed of PEG600 (CP6C12, LCP6LC12) (Table 4).

TABLE 4

Overview of SC-MBCP polymers.

| RCP | Type | Block 1 L/C ratio | Block 1 PEG MW | MW | Block 2 Type | Block ratio | IV (dl/g) |
|---|---|---|---|---|---|---|---|
| 1332 | LCP10LC20 | 2.5/97.5 | 1000 | 2000 | SC LL15/DL15 | 50/50 | 0.56 |
| 1585 | CP10C20 | 0/100 | 1000 | 2000 | SC LL20/DL20 | 70/30 | 0.82 |
| 15117 | LCP10LC20 | 2.5/97.5 | 1000 | 2000 | SC LL15/DL15 | 50/50 | 0.84 |
| 1631 | CP6C12 | 0/100 | 600 | 1200 | SC LL15/DL15 | 80/20 | 0.88 |
| 1616 | LCP6LC12 | 2/98 | 600 | 1200 | SC LL15/DL15 | 60/40 | 0.84 |
| 1617 | LCP6LC12 | 2/98 | 600 | 1200 | SC LL15/DL15 | 70/30 | 0.86 |
| 1633 | LCP6LC12 | 2/98 | 600 | 1200 | SC LL15/DL15 | 20/80 | 0.82 |
| 1620 | LCP6LC12 | 2/98 | 600 | 1200 | SC LL20/DL20 | 70/30 | 0.80 |
| 1622 | LCP6LC12 | 2798 | 600 | 1200 | SC LL20/DL20 | 80/20 | 0.84 |
| 1634 | LCP6LC12 | 2/98 | 600 | 1200 | SC LL20/DL20 | 90/10 | 0.90 |

TABLE 4-continued

Overview of SC-MBCP polymers.

| RCP | Block 1 | | | Block 2 | | Block ratio | IV (dl/g) |
| --- | --- | --- | --- | --- | --- | --- | --- |
| | Type | L/C ratio | PEG MW | MW | Type | | |
| 1619 | LCP10LC20 | 2/98 | 1000 | 2000 | SC LL20/DL20 | 70/30 | 0.81 |
| 1621 | LCP10LC20 | 2/98 | 1000 | 2000 | SC LL20/DL20 | 80/20 | 0.93 |

The synthesised L-MBCP, I-MBCP, SC-MBCP and D-MBCP polymers were evaluated for their processability (particle size distribution, microscopic appearance, stickiness, absence of agglomeration) into polymer-only microspheres. Polymers that were well processable into microspheres were further evaluated for their in, vitro erosion kinetics.

The particle size distribution of the microspheres was measured by laser diffraction. Microspheres were suspended in water until transmittance was within 70-90% and the particle size distribution of the suspension was determined within the range of 10 nm-5000 µm. The surface morphology of the microspheres was evaluated by scanning electron microscopy, using a JEOL JCM-5000 Neoscope. A small amount of microspheres was adhered to carbon conductive tape and coated with gold for 3 min. The sample was imaged using a 10 kV electron beam.

The in vitro erosion of non-loaded polymer-only microspheres were measured in 100 mM of phosphate buffer pH 7.4 (90-100 mg of microspheres in 10 ml). The samples were incubated at 37° C. At each sampling point, the microspheres were collected, freeze-dried and weighed.

Figure 2:
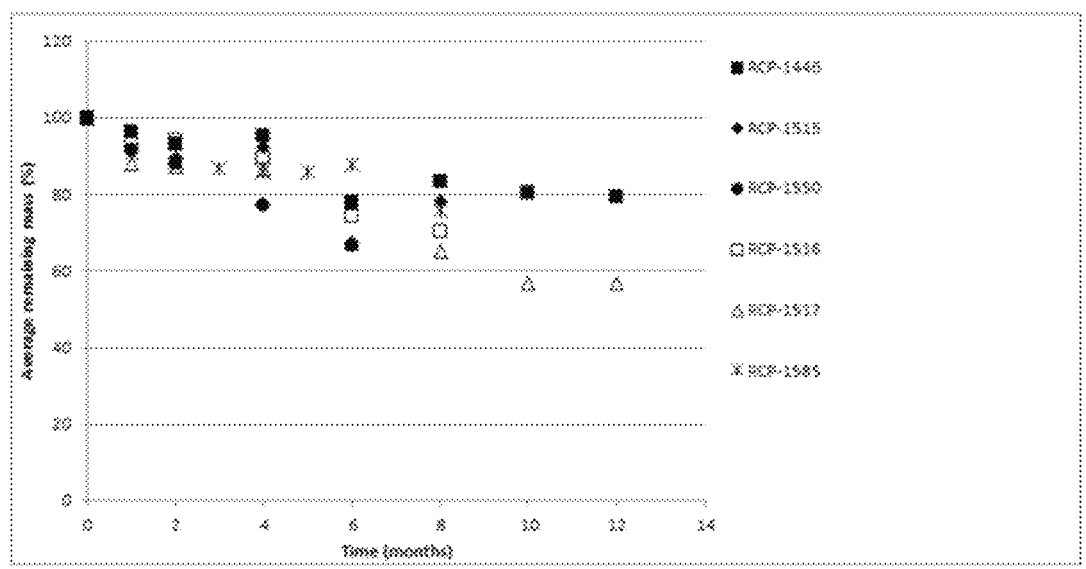
FIG. 2 In vitro erosion of microspheres composed of various L-MBCP, I-MBCP and SC-MBCP polymers. 50CP10C20-LL40 is included as reference.
Figure 3:
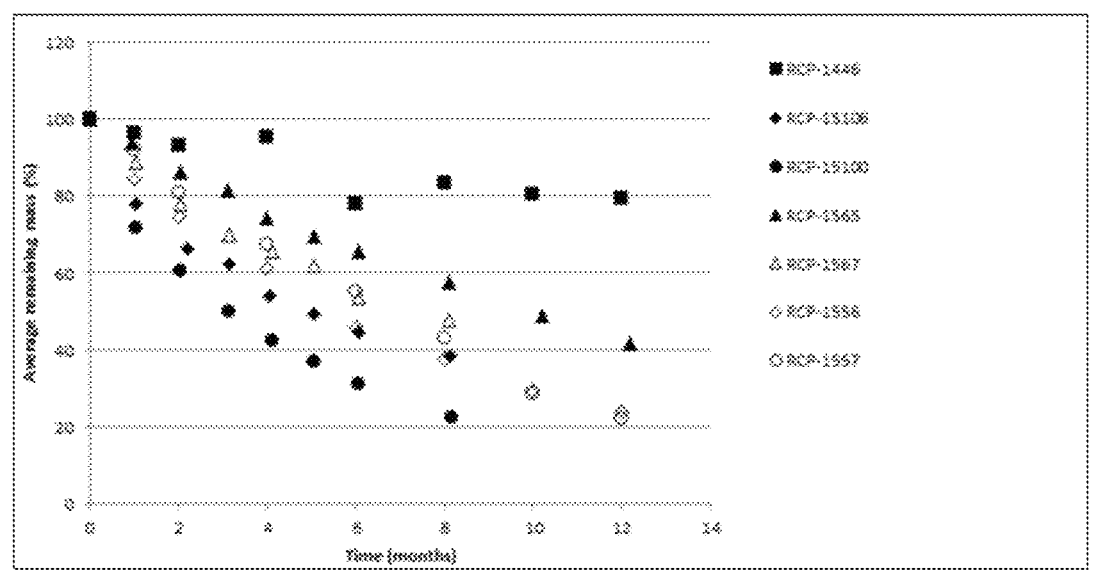
FIG. 3 In vitro erosion of microspheres composed of D-MBCP polymers containing various poly(ε-caprolactone)-PEG-poly(ε-caprolactone) based counter blocks. 50CP10C20-LL40 is included as reference.

The majority of the polymers were well processable allowing the manufacturing of microspheres with narrow particle size distribution. The polymers of the L-MBCP, I-MBCP and SC-MBCP families, however, showed very slow in, vitro erosion (FIG. 2). On the other hand, all multi-block copolymers based on a poly(Dioxanone) replacement of PLLA in the pre-polymer (B) segment in combination with a hydrophilic poly(ε-Caprolactone)-EEG-poly(e-Caprolactone) block (PCD multi-block copolymers) were found to erode significantly faster in vitro as compared to all other multi-block copolymers (FIG. 3).

The promising in vitro erosion characteristics of the PCD multi-block copolymers were attributed to the replacement of the poly(L-lactide)-based pre-polymer (B) segment by the poly(p-dioxanone) pre-polymer (B) segment.

In the following examples various biodegradable semi-crystalline, phase separated multi-block copolymers composed of a crystalline poly(p-dioxanone)-based hard pre-polymer (B) segment with a melting point ($T_m$) and a hydrophilic poly(ethylene glycol) (PEG)-based pre-polymer (A) segment having a glass transition temperature ($T_g$) below 37° C. under physiological conditions were synthesised and evaluated for their processing into drug-loaded microparticles and implants, drug release characteristics and erosion characteristics.

Example 2

This example describes the analytical methods used for the characterization of pre-polymers and multi-block copolymers. $^1$H-NMR was performed on a Bruker Avance DRX 500 MHz NMR spectrometer (B AV-500) equipped with Bruker Automatic Sample Changer (BACS 60) (Varian) operating at 500 MHz. The di waiting time was set to 20 s, and the number of scans was 16. Spectra were recorded from 0 to 14 ppm. Conversion was determined from $^1$H-NMR, pre-polymer $M_n$ was determined from in weights and $^1$H-NMR. $^1$H-NMR samples were prepared by adding 1.3 g of deuterated chloroform to 25 mg of polymer.

Intrinsic viscosity was measured using an Ubbelohde Viscosimeter (DIN), type OC. Si Analytics supplied with a Si Analytics Viscosimeter including a water bath. The measurements were performed in chloroform at 25° C. The polymer concentration in chloroform was such that the relative viscosity was in the range of 1.2-2.0.

p-Dioxane, ethanol and n-heptane content was determined using a GC-FID headspace method. Measurements were performed on a GC-FID Combi Sampler supplied with an Agilent Column, DB-624/30 m/0.53 mm. Samples were prepared in DMSO (dimethylsulphoxide). Residual solvent contents was determined using p-dioxane, ethanol and n-heptane calibration standards.

Modulated differential scanning calorimetry (MDSC) was used to determine the thermal behaviour of the multi-block copolymers using a Q2000 MDSC (TA instruments, Ghent. Belgium). About 5-10 mg of dry material was accurately weighed and heated under a nitrogen atmosphere from −85° C. to 120° C. at a heating rate of 2° C./min and a modulation amplitude of +/−0.42° C. every 80 seconds. The glass transition temperature ($T_g$, midpoint) and the melting temperature (maximum of endothermic peak, $T_m$) and the melting enthalpy ($\Delta H_m$), which was calculated from the surface area of the melting endotherm, were determined from the reversing heat flow. Temperature and enthalpy were calibrated with an indium standard.

Example 3

In this example, procedures for the preparation of poly (ε-caprolactone)-co-PEG-co-poly(ε-caprolactone) pre-polymer (A) are provided. The CL (CL=ε-caprolactone. Acros Organics) monomer was dried and distilled over $CaH_2$ under reduced pressure and stored under a nitrogen atmosphere until further use. Its quality was checked by $^1$H-NMR.

PEG was weighed into a three-necked bottle under nitrogen atmosphere and dried at 90° C. under reduced pressure for at least 16 h. CL was added to the PEG under nitrogen atmosphere and the mixture was heated to 160° C. Subsequently, stannous octoate (Sigma Corp.) was added at a monomer catalyst ratio of 5000 to 12 000 and the mixture was magnetically stirred and reacted at 160° C. until conversion was >98%.

Poly(ε-caprolactone)-co-$PEG_{1000}$-co-poly(ε-caprolactone) pre-polymer with a target $M_n$ of 2000 g/mol (abbreviated as ppCP10C20) was prepared by ring-opening polymerisation of e-caprolactone using polyethyleneglycol with a molecular weight of 1000 g/mol (PEG1000) as initiator. 500.9 g (2.00 mol) of PEG1000 (Merck, Emprove® Essential Ph Eur) was weighed into a three-necked bottle under nitrogen atmosphere and dried at 90° C.

for at least 16 h under reduced pressure. ε-Caprolactone (Acros Organics) was dried and distilled over CaH$_2$ under reduced pressure and stored under a nitrogen atmosphere. 495.9 g (4.34 mol) of e-caprolactone was added to the PEG under nitrogen atmosphere and the mixture was heated to 160° C. 140.1 mg of stannous octoate was added and the mixture was magnetically stirred and reacted at 160° C. during 73 h. $^1$H-NMR showed ~100% monomer conversion. Molecular weight as determined by $^1$H-NMR was 1980 g/mol.

Poly(ε-caprolactone)-co-PEG 1500-co-poly(ε-caprolactone) pre-polymer with a target M$_n$ of 2000 g/mol (abbreviated as ppCP15C20) was prepared similarly by ring-opening polymerisation of ε-caprolactone using polyethyleneglycol with a molecular weight of 1500 g/mol (PEG1500) as initiator. 152.6 g (0.10 mol) of PEG MW 1500 (Merck) was weighed into a three-necked bottle under nitrogen atmosphere and dried at 90° C. for at least 16 h under reduced pressure. 49.0 g (0.43 mol) of ε-caprolactone was added to the PEG under nitrogen atmosphere and the mixture was heated to 130° C. 31.3 mg of stannous octoate was added and the mixture was magnetically stirred and reacted at 130° C. during ~192 h. $^1$H-NMR showed 97.1% monomer conversion. Molecular weight as determined by $^1$H-NMR was 2000 g/mol.

Poly(ε-caprolactone)-co-PEG3000-co-poly(ε-caprolactone) pre-polymer with a target M$_n$ of 4000 g/mol (abbreviated as ppCP30C40) was prepared similarly by ring-opening polymerisation of ε-caprolactone using polyethyleneglycol with a molecular weight of 3000 g/mol (PEG3000) as initiator. 183.54 g (61.2 mmol) of PEG MW 3000 (Merck) was weighed into a three-necked bottle under nitrogen atmosphere and dried at 90° C. for at least 16 h under reduced pressure. 61.22 g (0.54 mol) of e-caprolactone was added to the PEG under nitrogen atmosphere and the mixture was heated to 160° C. 25.1 mg of stannous octoate was added and the mixture was magnetically stirred and reacted at 160° C. during ~69 h. $^1$H-NMR showed 99.4% monomer conversion. Molecular weight as determined by $^1$H-NMR was 3970 g/mol. Experimental details and results obtained for synthesis of poly(ε-caprolactone-co-PEG-co-poly(ε-caprolactone) pre-polymers are listed in Table 5.

of 200 g/mol (PEG200) as initiator. 450.7 g (3.95 mol) of D,L-lactide (Purac) was weighed into a three-necked bottle under nitrogen atmosphere and dried at 50° C. for at least 16 h under reduced pressure. 49.7 g (0.25 mol) of pre-dried PEG200 (Merck, EMPROVE® ESSENTIAL DAB 8) was added under a nitrogen atmosphere. The mixture was heated to 140° C. 59.6 mg of stannous octoate was added and the mixture was magnetically stirred and reacted at 140° C. during 69 h. $^1$H-NMR showed 95.4% monomer conversion. Molecular weight as determined by $^1$H-NMR was 2000 g/mol.

Poly(DL-lactide)-co-PEG600-co-poly(DL-lactide) pre-polymer with a target M$_n$ of 1200 g/mol (abbreviated as ppLP6L12) was prepared by ring-opening polymerisation of DL-lactide using polyethyleneglycol with a molecular weight of 600 g/mol (PEG600) as initiator. 252.4 g (2.21 mol) of D,L-lactide (Purac) was weighed into a three-necked bottle under nitrogen atmosphere and dried at 50° C. for at least 16 h under reduced pressure. 249.5 g (0.42 mol) of pre-dried PEG600 (Merck, EMPROVE® ESSENTIAL Ph Eur) was added under a nitrogen atmosphere. The mixture was heated to 140° C. 51.4 mg of stannous octoate was added and the mixture was magnetically stirred and reacted at 140° C. during 22 h. $^1$H-NMR showed 96.0% monomer conversion. Molecular weight as determined by $^1$H-NMR was 1190 g/mol.

Poly(DL-lactide)-co-PEG1000-co-poly(DL-lactide) pre-polymer with a target M$_n$ of 2000 g/mol (abbreviated as ppLP10L20) was prepared by ring-opening polymerisation of DL-lactide using polyethyleneglycol with a molecular weight of 1000 g/mol (PEG1000) as initiator. 256.2 g (2.24 mol) of D,L-lactide (Purac) was weighed into a three-necked bottle under nitrogen atmosphere and dried at 50° C. for at least 16 h under reduced pressure. 240.8 g (0.24 mol) of pre-dried PEG1000 (Merck, EMPROVE® ESSENTIAL Ph Eur) was added under a nitrogen atmosphere. The mixture was heated to 140° C. 71.1 mg of stannous octoate was added and the mixture was magnetically stirred and reacted at 140° C. during 190 h. $^1$H-NMR showed 95.4% conversion. Molecular weight as determined by $^1$H-NMR was 1920 g/mol.

Poly(ε-caprolactone-co-DL-lactide)-co-PEG 1000-co-poly(ε-caprolactone-co-DL-lactide) pre-polymer with a tar-

TABLE 5

Experimental details and results obtained for synthesis poly(ε-caprolactone-co-PEG-co-poly(ε-caprolactone) pre-polymers.

| Pre-polymer (A) | Target M$_n$ (g/mol) | PEG MW (g/mole) | CL (g) | PEG (g) | Stannous octoate (mg) | Conv. (%) | M$_n$* (g/mol) |
|---|---|---|---|---|---|---|---|
| ppCP10C20 | 2000 | 1000 | 495.9 | 500.9 | 140.1 | 100% | 1980 |
| ppCP15C20 | 2000 | 1500 | 49.00 | 152.6 | 31.3 | 97.1% | 2000 |
| ppCP30C40 | 4000 | 3000 | 61.22 | 183.5 | 25.1 | 99.4% | 3970 |

M$_n$* calculated by $^1$H-NMR

Example 4

In this example, procedures for the preparation of prepolymer (A) comprising poly(DL-lactide)-co-PEG-co-poly (DL-lactide), poly(ε-caprolactone-co-DL-lactide)-co-PEG 1000-co-poly(ε-caprolactone-co-DL-lactide) and poly(p-dioxanone)-co-PEG1000-co-poly(p-dioxanone) are provided.

Poly(DL-lactide)-co-PEG200-co-poly(DL-lactide) pre-polymer with a target M$_n$ of 2000 g/mol (abbreviated as ppLP2L20) was prepared by ring-opening polymerisation of DL-lactide using polyethyleneglycol with a molecular weight get M$_n$ of 2000 g/mol (abbreviated as ppLCP10LC20) was prepared by ring-opening copolymerisation of ε-caprolactone and DL-lactide (L/C=5/95 mol/mol) using polyethylene glycol with a molecular weight of 1000 g/mol (PEG1000) as initiator. 15.5 g (0.11 mol) of D,L-lactide (Purac) was weighed into a three-necked bottle under nitrogen atmosphere and dried at 50° C. for at least 16 h under reduced pressure. 248.5 g (0.25 mol) of pre-dried PEG 1000 (Merck, EMPROVE® ESSENTIAL Ph Eur), together with 233.0 g (2.04 mol) of freshly distilled ε-caprolactone was added under a nitrogen atmosphere. The mixture was heated to 140° C. 69.8 mg of stannous octoate was added and the mixture was magnetically stirred and reacted at 140° C. during 120 h. $^1$H-NMR showed 98.8% monomer conversion. Molecular weight as determined by $^1$H-NMR was 1980 g/mol.

Poly(p-dioxanone)-co-PEG1000-co-poly(p-dioxanone) with a target $M_n$ of 2400 g/mol (abbreviated as ppDP10D24) was prepared by ring opening polymerisation of p-dioxanone using polyethylene glycol with molecular weight of 1000 g/mol (PEG1000) as initiator. 5.84 g (57.2 mmol) of freshly distilled p-dioxanone was added to 4.17 g (4.17 mmol) of pre-dried PEG1000 (Merck, EMPROVE® ESSENTIAL Ph Eur) in a three-necked flask and the reaction mixture was heated to 80° C. 4.1 mg of stannous octoate was added and the mixture was magnetically stirred and reacted at 80° C. during 265 h. $^1$H-NMR showed 75.1% monomer conversion. Molecular weight as determined by $^1$H-NMR was 2410 g/mol.

Experimental details and results obtained for synthesis of the pre-polymers are listed in Table 6.

TABLE 6

Experimental details and results obtained for synthesis of poly(DL-lactide)-co-PEG-co-poly(DL-lactide), poly(ε-caprolactone-co-DL-lactide)-co-PEG1000-co-poly(ε-caprolactone-co-DL-lactide) and poly(p-dioxanone)-co-PEG1000-co-poly(p-dioxanone) pre-polymers.

| Pre-polymer (A) | Target $M_n$ (g/mol) | PEG MW (g/mol) | D,L-LA (g) | CL (g) | PDO (g) | PEG (g) | SnOct (mg) | Conv. (%) | $M_n$* (g/mol) |
|---|---|---|---|---|---|---|---|---|---|
| ppLP2L20 | 2000 | 200 | 450.7 | N.A. | N.A. | 49.7 | 59.6 | 95.4 | 2000 |
| ppLP6L12 | 1200 | 600 | 252.4 | N.A. | N.A. | 249.5 | 51.4 | 96.0 | 1190 |
| ppLP10L20 | 2000 | 1000 | 256.2 | N.A. | N.A. | 240.8 | 71.1 | 95.4 | 1920 |
| ppLCP10LC20 (L/C = 5/95) | 2000 | 1000 | 15.5 | 233.0 | 248.5 | 49.7 | 61.2 | 95.4 | 2000 |
| ppDP10D24 | 2400 | 1000 | N.A. | N.A. | 5.84 | 4.17 | 4.17 | 75.1 | 2410 |

$M_n$* calculated by $^1$H-NMR;
N.A.—not applicable

Example 5

Poly(p-dioxanone) pre-polymer with different molecular weights were synthesised in the bulk by 1,4-butanediol (BDO) initiated ring-opening polymerisation. BDO (Acros Organics) and p-dioxanone monomer (PDO, ≥99.5% pure. HBCChem) were distilled over $CaH_2$ under reduced pressure and stored under nitrogen atmosphere until further use. PDO was molten and introduced into a jacketed reactor under nitrogen atmosphere. Then BDO was added to the PDO under nitrogen atmosphere. The mixture was heated to 80° C. giving a clear molten fluid. Stannous octoate (Sigma-Aldrich) was added as a solution in p-dioxane (Acros, dried and distilled) at a monomer catalyst ratio of 23 000 to 33 000, starting the ring-opening polymerisation. The mixture was mechanically stirred at 80° C. Upon solidification of poly(p-dioxanone) stirring was stopped. In the solid state polymerisation continued and conversion increased to the targeted 80-90%. Table 7 lists the amounts of PDO monomers, BDO initiator, and stannous octoate catalyst used for the synthesis of poly(p-dioxanone) pre-polymers with different molecular weight. Samples were taken from the bulk of the solidified polymer and analysed by $^1$H-NMR as to determine the average conversion and molecular weight of the polymers. Polymerisation was continued until conversion was ≥80% and varied from 80.0 to 92.7%. The number averaged molecular weights of the so-prepared poly(p-dioxanone) pre-polymers (ppDxx) varied from 1783-2806 g/mol. Poly(p-dioxanone) pre-polymers were not isolated, but left in the reactor until further use.

TABLE 7

Experimental details and results obtained for synthesis poly(p-dioxanone) pre-polymers.

| Pre-polymer (B) | Batch nr | Target $M_n$ (g/mol) | PDO (g) | BDO (g) | Stannous octoate (mg) | Conv. (%) | $M_n$* (g/mol) |
|---|---|---|---|---|---|---|---|
| ppD20 | 1505 | 2000 | 59.13 | 2.21 | 7.7 | 80.0 | 1783 |
| ppD23 | 1551 | 2300 | 45.26 | 1.57 | 76.6 | 85.6 | 2043 |
| ppD25 | 1542 | 2500 | 182.64 | 6.24 | 232.4 | 92.7 | 2401 |
| ppD28 | 1716 | 2800 | 189.25 | 5.30 | 19.8 | 86.9 | 2806 |

$M_n$* calculated by $^1$H-NMR

Example 6

This example describes the synthesis and characterization of [poly(ε-caprolactone)-co-PEG-co-poly(ε-caprolactone)]-b-[poly(p-dioxanone)] multi-block copolymers.

[Poly(ε-caprolactone)-co-PEG-co-poly(ε-caprolactone)]-b-[poly(p-dioxanone)] multi-block copolymers with various block ratios were prepared by chain-extension of ppDxx pre-polymer with ppCP10C20, ppCP15C20 or ppCP30C40 pre-polymers using 1,4-butanediisocyanate as a chain extender. First a ppDxx pre-polymer was prepared in situ in a jacketed reactor as described above where after the required amount of ppCP10C20, ppCP15C20 or ppCP30C40 pre-polymer prepared as described above was added. Water-free p-dioxane (Acros Organics, distilled and fractionated under reduced pressure in a modified rotary evaporator setup) was pumped into the reactor until a polymer concentration of 30 wt. % was reached. The reactor was heated to 80° C. to dissolve the pre-polymers and 1,4-butanediisocyanate (Bayer) was added. Additional stannous octoate was added to increase its total content to 45 ppm and the reaction mixture was stirred magnetically until the desired viscosity was obtained, where after distilled p-dioxane containing 20 wt. % water was added to quench unreacted isocyanate groups and stop the reaction. Stirring was continued for an additional 30 minutes. The reaction mixture was further diluted with p-dioxane to a polymer concentration of 10 wt. %, cooled to room temperature, poured into a tray and frozen at −18° C. p-Dioxane was removed from the frozen reaction solution under reduced pressure in a vacuum oven at 30° C. or by precipitation using a mixture of ethanol and n-heptane. Table 8 lists the experimental details of the various [poly(ε-caprolactone)-co-PEG-co-poly(ε-caprolactone)]-b-[poly(p-dioxanone)] multi-block copolymers.

TABLE 8

Synthesis details of [poly(ε-caprolactone)-co-PEG-co-poly(ε-caprolactone)]-b-[poly(p-dioxanone)] multi-block copolymers.

| Grade | RCP | ppDxx (g) | ppDxx $M_n$ (g/mol) | ppCPxxCyy (g) | ppCPxxCyy $M_n$ (g/mol) | BDI (g) |
|---|---|---|---|---|---|---|
| 54CP10C20-D18 | 1510 | 48.74 | 1783 | 48.89 | 2000 | 6.7745 |
| 60CP10C20-D23 | 15126 | 39.28 | 2260 | 59.11 | 2041 | 6.4166 |
| 30CP15C20-D24 | 1567 | 53.57 | 2437 | 28.96 | 2000 | 5.1712 |
| 50CP15C20-D23 | 15125 | 49.89 | 2294 | 50.03 | 2000 | 6.4685 |
| 50CP15C20-D25 | 1579 | 50.58 | 2547 | 49.70 | 2000 | 6.2321 |
| 50CP30C40-D28 | 1524 | 59.11 | 2790 | 54.90 | 3091 | 4.8497 |

Polymers were stored in a sealed package at −18° C. and analysed for polymer composition ($^1$H-NMR), intrinsic viscosity, residual p-dioxane content (gas chromatography) and thermal properties (mDSC) as described above.

Table 9 shows the collected analysis results for 54CP10C20-D20, 60CP10C20-D23, 50CP15C20-D23, and 50CP15C20-D25. The actual composition of the copolymers, as determined by $^1$H-NMR from D/P and C/P molar ratios resembled the target composition well. The intrinsic viscosity of the polymers varied between 0.54 and 1.13 dl/g. Residual dioxane contents were very low indicating effective removal thereof by vacuum-drying and precipitation.

TABLE 9

Collected results regarding the chemical composition, intrinsic viscosity and residual dioxane content of multi-block copolymers

| Grade | RCP | Molar CL/P ratio in-weight | Molar CL/P ratio $^1$H-NMR | Molar D/P ratio in-weight | Molar D/P ratio $^1$H-NMR | IV (dL/g) | Dioxane content (ppm) |
|---|---|---|---|---|---|---|---|
| 54CP10C20-D18 | 1510 | 8.6 | 8.7 | 16.6 | 18.8 | 0.54 | <88 |
| 60CP10C20-D23 | 15126 | 9.0 | 8.8 | 11.5 | 12.8 | 0.98 | <92 |
| 30CP15C20-D24 | 1567 | 4.3 | 4.4 | 35.1 | 35.8 | 0.63 | <104 |
| 50CP15C20-D23 | 15125 | 4.3 | 4.2 | 17.2 | 18.9 | 1.13 | <92 |
| 50CP15C20-D25 | 1579 | 4.2 | 4.2 | 20.8 | 19.3 | 0.94 | <102 |
| 50CP30C40-D28 | 1524 | 8.0 | 8.0 | 37.7 | 41.0 | 1.2 | <110 |

Figure 4A:
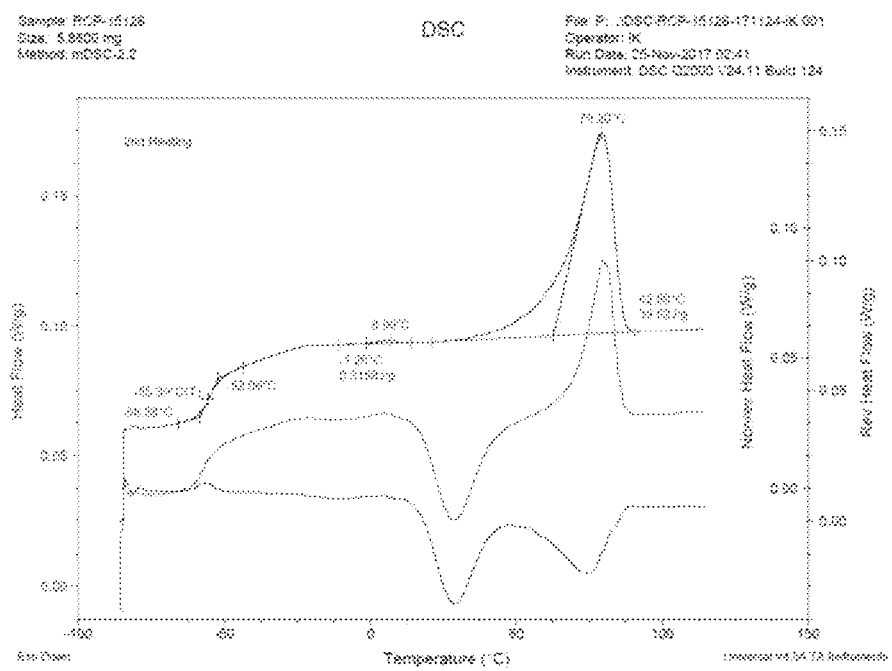
FIG. 4 DSC thermograms of [poly(ε-caprolactone)-co-PEG-co-poly(ε-caprolactone)]-b-[poly(p-dioxanone)] multi-block copolymers: RCP-15126 (panel A), RCP-15125 (panel B) and RCP-1524 (panel C) multi-block copolymers.
Figure 4B:
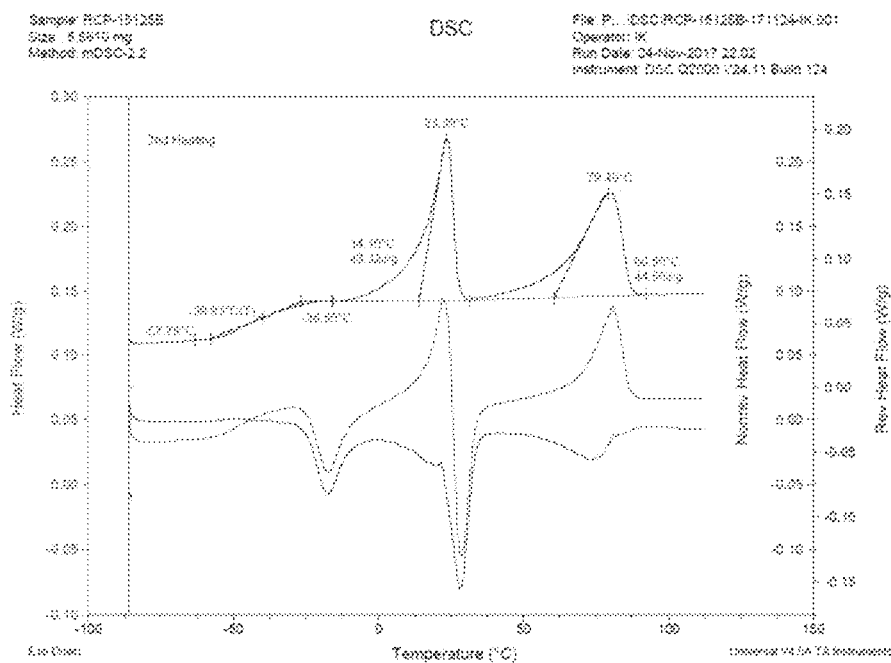
Figure 4C:
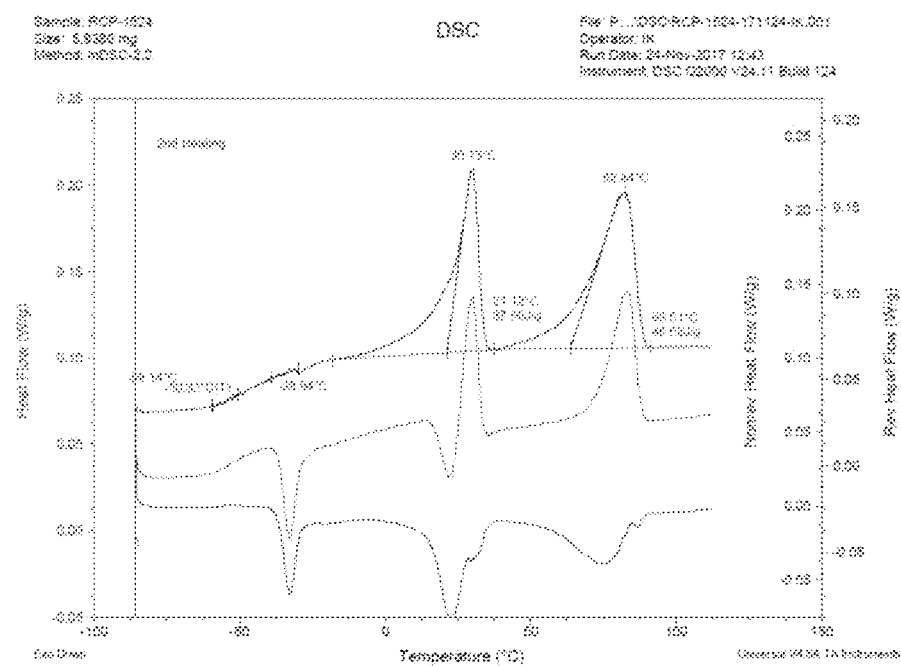
Figure 5A:
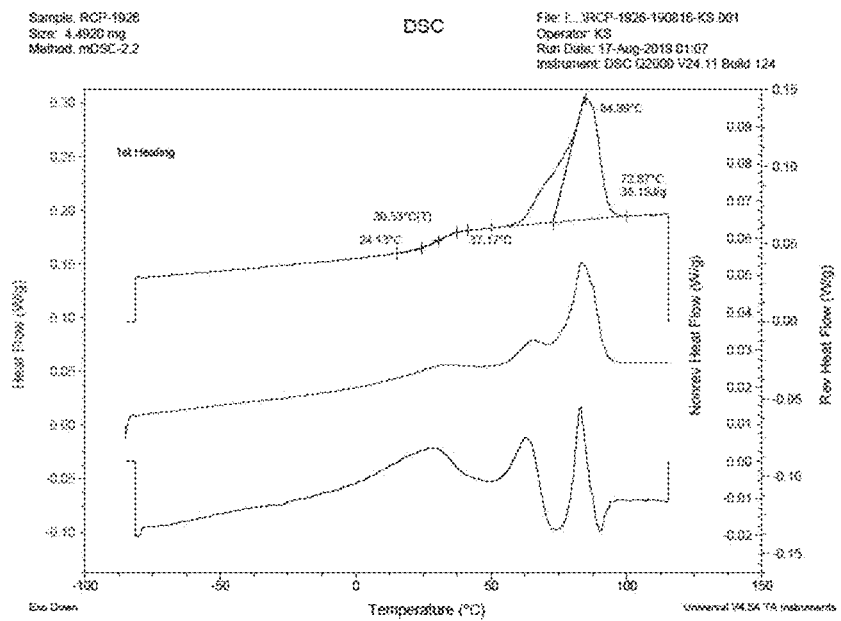
FIG. 5 DSC thermograms of 60LP2L20-D27 (RCP 1926) (panel A), 10LP6L12-D27 (RCP 1804) (panel B), 10LP10L20-D27 (RCP 1810) (panel C) and 50DP10D24-D25 (RCP 1509) (panel D) multi-block copolymers.
Figure 5B:
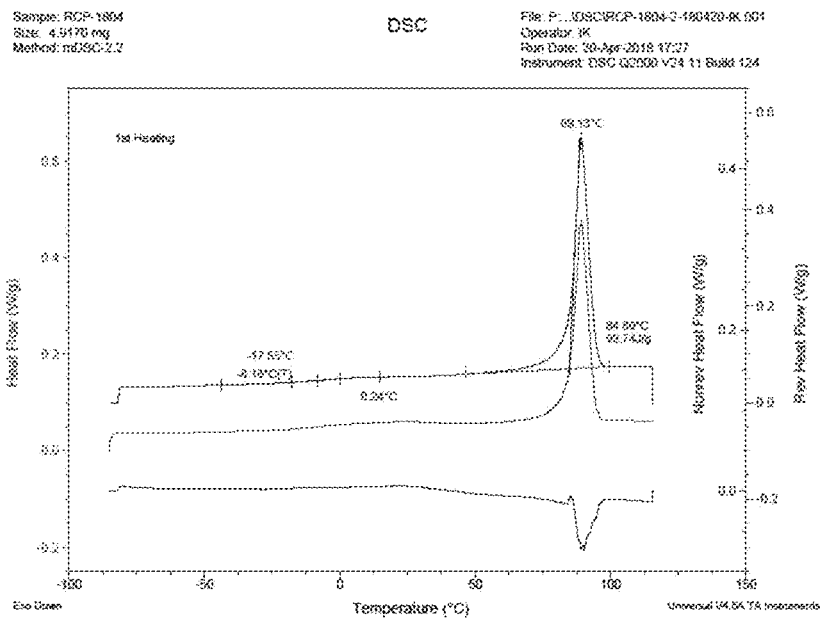
Figure 5C:
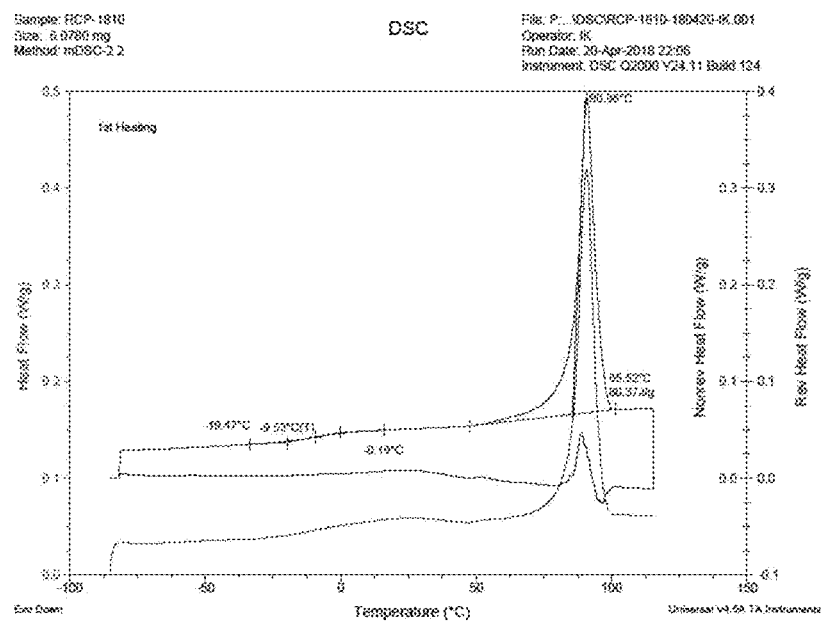
Figure 5D:
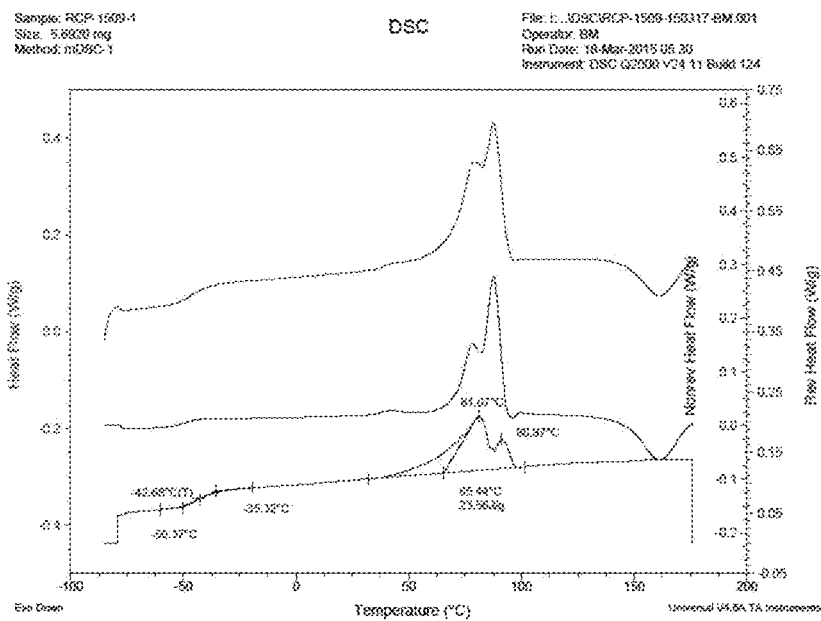

The multi-block copolymers were analysed for their thermal properties to confirm their phase separated morphology (Table 10). FIG. 4 shows typical DSC thermograms of 60CP10C20-D23 (RCP 15126) (panel A), 50CP15C20-D23 (RCP 15125) (panel B) and 50CP30C40-D28 (RCP 1524) (panel C) multi-block copolymers. All multi-block copolymers exhibited a melting temperature ($T_m$) at approximately 80° C. due to melting of the dioxanone segment. Additionally, in PEG1500-containing 50CP15C20-D23 and PEG3000-containing 50CP30C40-D28 a melting peak is found at about 50° C. due to melting of the PEG-rich phase. The glass transition temperature ($T_g$) of the multi-block copolymers is in general in between that of the two pre-polymers, indicating phase mixing of the amorphous pre-polymer with the amorphous content of the semi crystalline pre-polymer.

TABLE 10

Thermal characteristics of multi-block copolymers (MBCP).

| RCP | Grade | $T_g$ (° C.) | $T_{m,1}$ (° C.) | $\Delta H_{m,1}$ ($T_{m1}$) (J/g) | $T_{m,2}$ (° C.) | $\Delta H_{m,2}$ (J/g) |
|---|---|---|---|---|---|---|
| 1510 | 54CP10C20-D18 | −61 | N.D. | N.D | 72.0 | 37.0 |
| 15126 | 60CP10C20-D23 | −55.4 | 6.9 | 0.3 | 79.2 | 39.6 |
| 1567 | 30CP15C20-D24 | −53 | 11 | N.D. | 84.0 | 66.0 |
| 15125 | 50CP15C20-D23 | −39.9 | 23.4 | 43.3 | 79.5 | 44.6 |
| 1579 | 50CP15C20-D25 | −48.6 | 23.8 | 41.7 | 88.1 | 65.2 |
| 1524 | 50CP30C40-D28 | −50.3 | 30.1 | 37.5 | 82.4 | 46.6 |

N.D.: not detected;

Example 7

This example describes the synthesis and characterisation of [poly(DL-lactide)-co-PEG-co-poly(DL-lactide)]-b-[poly(p-dioxanone)] multi-block copolymers.

[poly(DL-lactide)-co-PEG-co-poly(DL-lactide)]-b-[poly(p-dioxanone)] multi-block copolymers with various block ratios were prepared by chain-extension of ppDxx pre-polymer with ppLP2L20, ppLP6L12 or ppLP10L20 pre-polymers using 1,4-butanediisocyanate as a chain extender. First a poly(p-dioxanone) pre-polymer was prepared in situ in a jacketed reactor as described above where after the required amount of ppLP2L20, ppLP6L12 or ppLP10L20 pre-polymer prepared as described above was added. Chain extension and work-up of the [poly(DL-lactide)-co-PEG-co-poly(DL-lactide)]-b-[poly(p-dioxanone)] multi-block copolymers was performed according to the procedures as described in Example 6. p-Dioxane was removed by precipitation using a mixture of ethanol and n-heptane. Table 11 lists the experimental details of the various [poly(DL-lactide)-co-PEG-co-poly(DL-lactide)]-b-[poly(p-dioxanone)] multi-block copolymers.

TABLE 11

Synthesis details of multi-block copolymers compose of poly(p-dioxanone) blocks in combination with various counter blocks.

| Grade | RCP | ppDxx (g) | ppDxx $M_n$ (g/mol) | ppLPxxLyy (g) | ppLPxxLyy $M_n$ (g/mol) | BDI (g) |
|---|---|---|---|---|---|---|
| 60LP2L20-D27 | 1926 | 173.86 | 2728 | 260.87 | 2000 | 25.98 |
| 10LP6L12-D27 | 1804 | 354.98 | 2665 | 39.65 | 1190 | 21.43 |
| 10LP10L20-D27 | 1810 | 354.23 | 2622 | 40.39 | 1920 | 20.02 |
| 60LCP10LC20-D25 | 1566 | 39.52 | 2436 | 59.10 | 1980 | 6.39 |
| 50DP10D24-D25 | 1509 | 9.69 | 2510 | 9.50 | 2410 | 0.89 |

Polymers were stored in a sealed package at −18° C. and analysed for polymer composition ($^1$H-NMR), intrinsic viscosity, residual p-dioxane content (gas chromatography) and thermal properties (mDSC) as described above.

copolymer. The synthesis of the polymers that were examined for their in, vitro erosion kinetics was described in Example 6. The composition and relevant physicochemical characteristics of the polymers are listed in Table 14.

TABLE 14

Composition and physicochemical characteristics of the poly(p-dioxanone)-based multi-block copolymers

| | | ppCPxxCyy-block | | | | ppDxx block | |
|---|---|---|---|---|---|---|---|
| Polymer grade | RCP | Mn ppCPxCz (g/mol) | PEG MW | PEG content | PCL length (g/mol) | $M_n$ ppDx (g/mol) | IV (dl/g) |
| 57CP10C20-D28 | 1502 | 2000 | 1000 | 28.5% | 500 | 2767 | 1.43 |
| 35CP15C20-D24 | 1567 | 2000 | 1500 | 26.3% | 250 | 2437 | 0.63 |
| 50CP15C20-D24 | 1556 | 2000 | 1500 | 37.5% | 250 | 2405 | 0.95 |
| 20CP30C40-D23 | 1557 | 4000 | 3000 | 15% | 500 | 2259 | 0.80 |
| 60CP10C20-D25 | 1565 | 2000 | 1000 | 30% | 500 | 2495 | 0.77 |
| 60CP10C12.5-D22 | 15100 | 1250 | 1000 | 48% | 62 | 2241 | 0.91 |
| 60CP10C16.7-D24 | 15102 | 1670 | 1000 | 36% | 335 | 2401 | 0.89 |

The actual composition of the copolymers, as determined by $^1$H-NMR from DIP and LIP molar ratios resembled the target composition well. The intrinsic viscosity of the polymers varied between 0.60 and 0.68 dl/g.

The multi-block copolymers were analysed for their thermal properties to confirm their phase separated morphology (Table 13). FIG. 5 shows typical DSC thermograms of 60LP2L20-D27 (RCP 1926) (panel A), 10LP6L12-D27 (RCP 1804) (panel B), 10LP10L20-D27 (RCP 1810) (panel C) and 50DP10D24-D25 (RCP 1509) (panel D) multi-block copolymers. All multi-block copolymers exhibited a melting temperature ($T_m$) between 85 and 90° C., due to melting of the poly(p-dioxanone) segment. The glass transition temperature ($T_g$) of the multi-block copolymers is in general in between that of the two pre-polymers, indicating phase mixing of the amorphous pre-polymer with the amorphous content of the semi crystalline pre-polymer.

TABLE 13

Thermal characteristics of multi-block copolymers (MBCP).

| RCP | Grade | $T_g$ (° C.) | $T_{m,1}$ (° C.) | $\Delta H_{m,1}$ ($T_{m1}$) (J/g) | $T_{m,2}$ (° C.) | $\Delta H_{m,2}$ (J/g) |
|---|---|---|---|---|---|---|
| 1926 | 60LP2L20-D27 | 30.5 | N.D. | N.D | 85.0 | 38.2 |
| 1804 | 10LP6L12-D27 | −8.2 | N.D. | N.D. | 89.1 | 99.7 |
| 1810 | 10LP10L20-D27 | −9.5 | N.D. | N.D. | 91.0 | 80.4 |
| 1566 | 60LCP10LC20-D25 | N.M. | N.M. | N.M. | N.M. | N.M. |
| 1509 | 50DP10D24-D25 | −42.68 | N.D. | N.D. | 91.0 | 23.56 |

N.D.: not detected;
N.M.: not measured;

Example 8

Due to the phase-separated morphology of the multi-block copolymers, the composition of the blocks significantly affects the overall erosion kinetics of the multi-block copolymers. The content and molecular weight of PEG as well as the length of the poly(ε-caprolactone) chains of the hydrophilic pre-polymer segment (A) and the molecular weight ($M_n$) of the crystalline poly(p-dioxanone) pre-polymer segment (B) are considered the most critical parameters for the overall erosion kinetics of the resulting multi-block copolymer.

Polymer-only microspheres were prepared by a solvent extraction/evaporation based oil-in-water emulsification process. 5.8 g of polymer dissolved in 52.4 g of dichloromethane (10.0 wt. %) was emulsified in 3.08 kg of ultrapure water containing 4.0 wt. % PVA and 5 wt. % NaCl via membrane emulsification using a membrane with a pore size of 20 μm. The resulting microspheres were collected on a 5 μm membrane filter and washed three times with 250 ml of ultrapure water containing 0.05 wt. % of Tween® 80 and three times with 250 g of ultrapure water. Finally, the microspheres were lyophilised. Particle size measurement and microscopic examination by SEM imaging were carried out following the same procedures as described in Example 1.

The in vitro erosion of non-loaded polymer-only microspheres was measured in 100 mM of phosphate buffer pH 7.4 (90-100 mg of microspheres in 10 ml). The samples were incubated at 37° C. At each sampling point, the microspheres were collected, freeze-dried and weighed.

Figure 6:
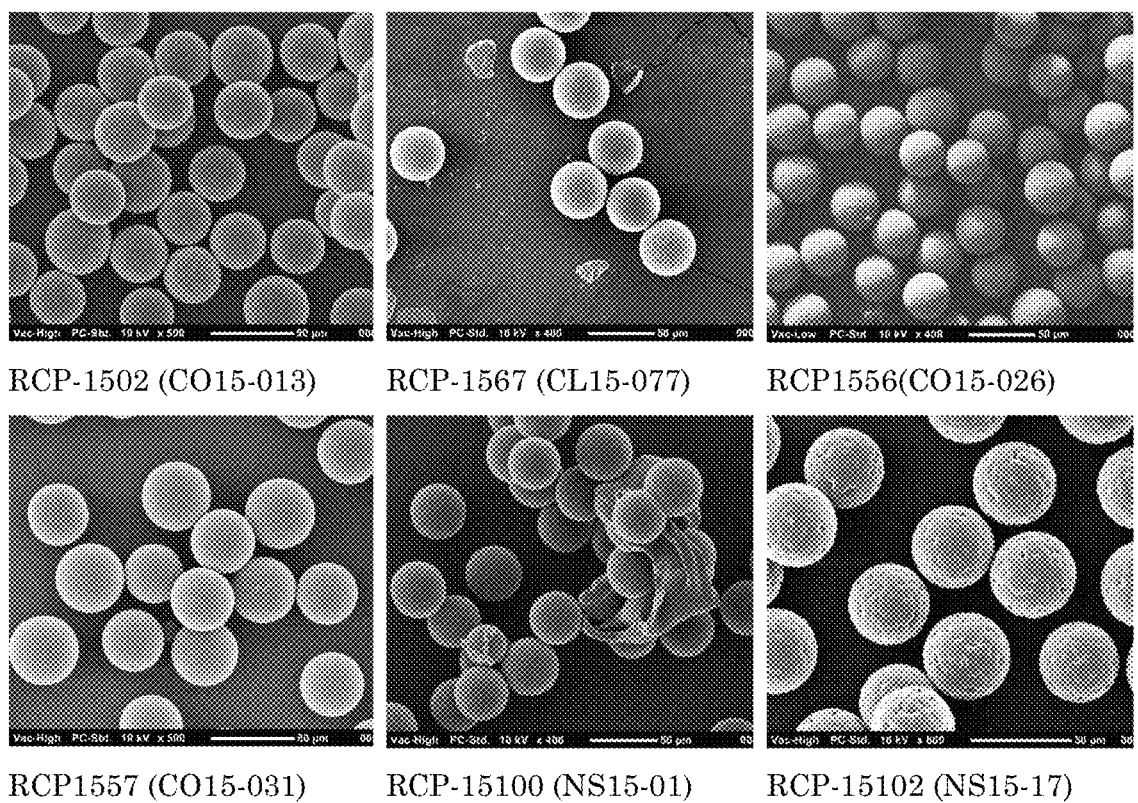
FIG. 6 SEM images of the different polymer-only microsphere batches, prepared with polyp-dioxanone) based multi-block copolymers with different composition of the hydrophilic block (PEG $M_n$, PEG content, poly(ε-caprolactone) chain length and block ratio).
Figure 7:
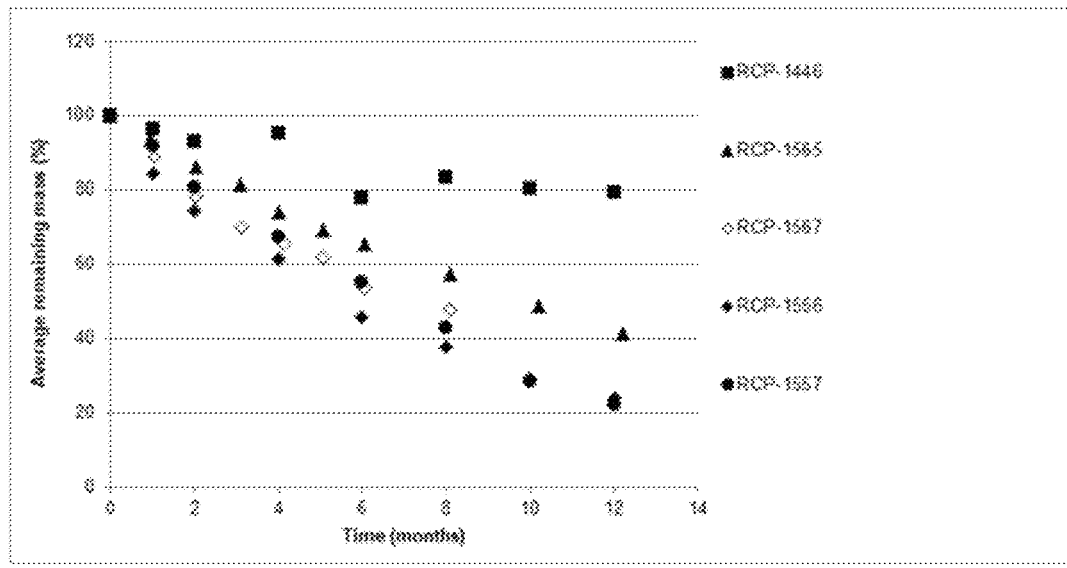
FIG. 7 In vitro erosion kinetics of polymer-only microspheres composed of 57CP10C20-D28, 35CP15C20-D24, 50CP15C20-D24, 20CP30C40-D23 (50CP10C20-LL40 was used as reference).

The various poly(p-dioxanone)-based multi-block copolymers were all well processable into microspheres. For all polymers spherical microspheres with a smooth surface morphology (FIG. 6) and an average size varying from 42 to 55 μm were obtained. FIG. 7 shows the effect of PEG molecular weight and PEG content of the hydrophilic block as well as the block ratio on in vitro erosion of D-MBCP-based polymer-only microspheres. Polymer-only microspheres composed of 50CP10C20-LL40 were included as reference material. The erosion rate of all multi-block copolymers composed of poly(p-dioxanone)-based crystalline blocks was significantly faster as compared to 50CP10C20-LL40. After 12 months the remaining mass of polymer-only microspheres composed of 50CP10C20-LL40 was approximately 80%. By replacing the LL40 block by a poly(p-dioxanone)-based block significantly faster eroding polymers were obtained. The remaining mass of polymer-only microspheres composed of 60CP10C20-D25 was around 40% after 12 months. By replacing PEG1000 by PEG1500 or PEG3000 the erosion rate could be further increased. Polymer-only microspheres composed of 30CP15C20-D24, 50CP15C20-D23 and 20CP30C40-D23 exhibited almost linear erosion kinetics with only 20-25% remaining mass after 12 months.

Figure 8:
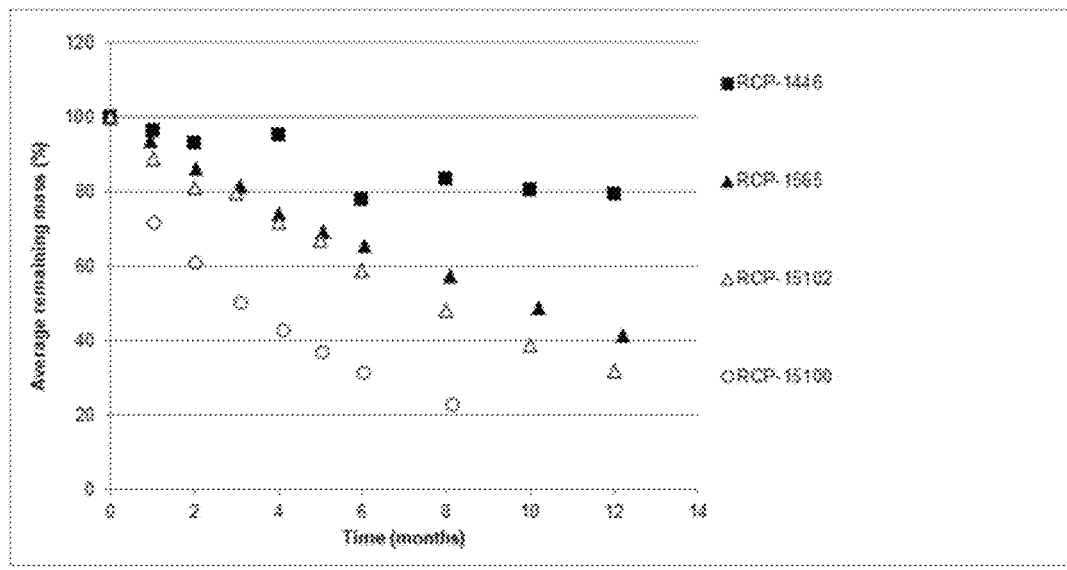
FIG. 8 Effect of molecular weight of poly(ε-caprolactone) chains on in vitro erosion of several poly(p-dioxanone) based multi-block copolymers (50CP10C20-LL40 was used as reference).

Furthermore, the erosion rate of the overall multi-block copolymers was found to increase significantly with decreasing length of the poly(ε-caprolactone) chains of the hydrophilic block (FIG. 8). This is attributed to the higher PEG content (and higher water-swellability) of the multi-block copolymers composed of hydrophilic blocks containing shorter poly(ε-caprolactone) chains.

Example 9

For the purpose of screening for poly(p-dioxanone)-based multi-block copolymers the in vitro erosion (IVE) kinetics of polymer-only microspheres composed of poly(p-dioxanone)-based multi-block copolymers with different compositions (synthesised as described in Example 6) were compared. Polymer-only microspheres were prepared and analysed for their in vitro erosion kinetics as described in Example 1. Table 15 shows in vitro erosion duration of polymer-only microspheres composed of different poly(p-dioxanone)-based multi-block copolymers.

TABLE 15

In vitro polymer erosion duration of various poly(p-dioxanone)-based multi-block copolymers.

| Multi-block copolymer | Polymer batch | In vitro erosion duration (IVE) [a] |
|---|---|---|
| 50CP10020-LLA0 | RCP-1312 /1446A | 3-4 yrs |
| 57CP10020-D23 | idT 1502 | 16 mths |
| 40CP10C12.5-D23 | RCP-15106 | 11 mths |
| 40CP10C16 7-D23 | RCP-15108 | 16 mths |
| 50CP10014.3-D23 | RCP-15104 | 12 mths |
| 60CP10012.5-D23 | RCP-15100 | 9 mths |
| 60CP10016.7-D23 | RCP-15102 | 15 mths |
| 30CP15C20-D24 | RCP-1567 | 10 mths |
| 50CP15C20-D23 | RCP-1556 | 13 mths |
| 30CP15030-D23 | RCP-15103 | 14 mths |
| 30CP15050-D23 | RCP-15101 | 16 mths |
| 40CP15037 5-1)23 | RCP-15110 | 18 mths |
| 50CP15C30-D23 | RCP-15109 | 18 mths |
| 50CP15050-D23 | RCP-15107 | 24 mths |
| 20CP30040-D25 | RCP-1557 | 13 mths |

[a] Determined by linear extrapolation of the remaining mass curve to 10 % of remaining mass. Each in vitro erosion experiment was performed for at least 8 months.

All poly(p-dioxanone)-based multi-block copolymers degraded much faster than the 50CP10C20-LL40 reference material. Based on extrapolation of the in vitro erosion data, the time for complete in vitro erosion of the various poly(p-dioxanone)-based multi-block copolymers varied from 9 to 24 months, which is 2 to 5 times faster than obtained for 50CP10C20-LL40. The time for complete in vivo erosion of the various poly(p-dioxanone)-based multi-block copolymers is expected to vary from 3 to 8 months.

Example 10

Figure 9:
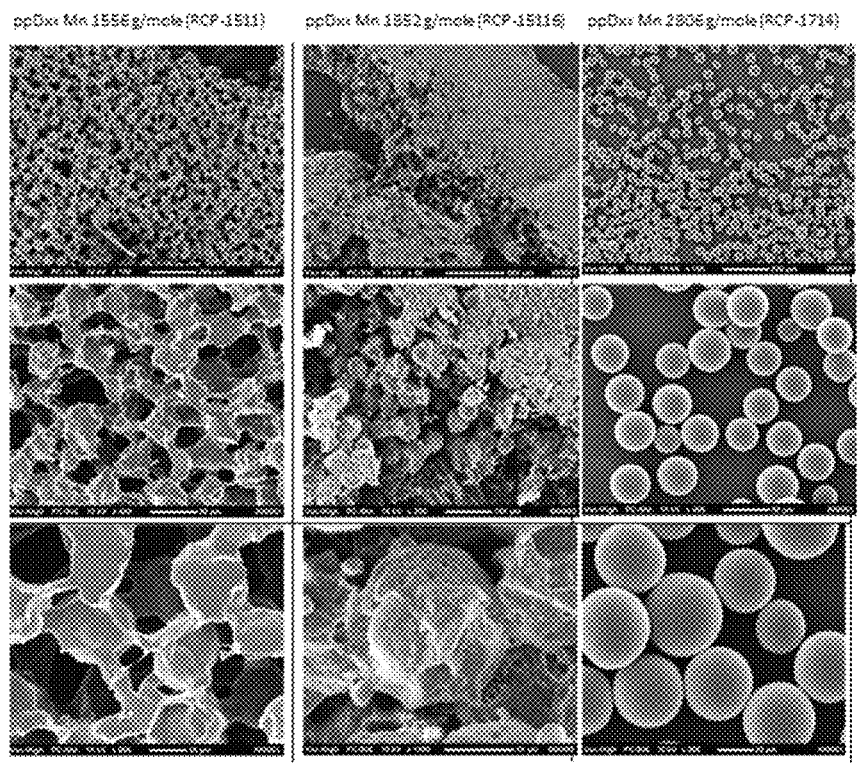
FIG. 9 SEM photographs of polymer-only microspheres prepared of 60CP10C20-Dxx multi-block copolymers composed of poly(p-dioxanone)-blocks with different molecular weight ($M_n$).

To further characterise the 60CP10C20-Dxx based microspheres the effect of $M_n$ of the poly(p-dioxanone) pre-polymer block of 60CP10C20-Dxx on microsphere processability and crystallisation of the poly(p-dioxanone) block was investigated in more detail. 60CP10C20-Dxx multi-block copolymers composed of poly(p-dioxanone) pre-polymer blocks with $M_n$ varying from 1556 g/mol to 2806 g/mol (Table 19) were synthesised as described in Example 6. Polymer-only microspheres were prepared and analysed for particle size and microscopic appearance as described in Example 1. Microspheres prepared of RCP1511 ($M_n$ D-block 1556 g/mol) and RCP15116 ($M_n$ D-block 1852 g/mol) exhibited poor processability (formation of polymer threads, smearing) yielding sticky microspheres that showed severe agglomeration (Table 16. FIG. 9). Microspheres prepared of 60CP10C20-Dxx multi-block copolymers composed of D-blocks with $M_n$ exceeding 2200 g/mol (RCP 1721, RCP 1711, RCP 1720 and RCP 1714) exhibited excellent processability yielding spherical microspheres with a smooth surface and no visible surface porosity and exhibited good powder flowability without any tendency to agglomerate.

Thermal characteristics of the microspheres were analysed by modulated differential scanning calorimetry (m-DSC) using a Q2000 DSC (TA Instruments) as described in Example 1. For the polymers, the melting temperature ($T_m$) and corresponding melting enthalpy ($\Delta H_m$) of the semi-crystalline poly(p-dioxanone) blocks were determined from the reversing heat flow. For the polymer-only microspheres, $T_m$ and $\Delta H_m$ were determined from the total heat flow of the first heating run.

Figure 10:
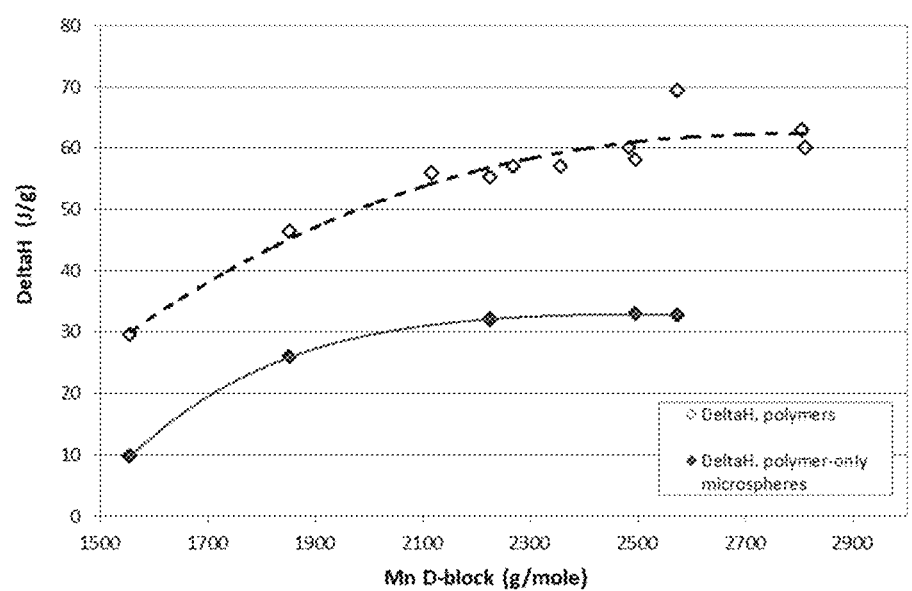
FIG. 10 Effect of molecular weight ($M_n$) of the poly(p-dioxanone) pre-polymer block on the melting enthalpy of 60CP10C20-Dxx multi-block copolymers and polymer-only microspheres composed thereof.

Thermal analysis showed that polymer-only microspheres prepared of 60CP10C20-Dxx composed of poly(p-dioxanone) pre-polymer blocks with low $M_n$ (RCP 1511, RCP 15116) had a significantly lower melting temperature and melting enthalpy as compared to polymer-only microspheres prepared of 60CP10C20-Dxx multi-block copolymers composed of poly(p-dioxanone) pre-polymer blocks with $M_n$ exceeding 2200 g/mol (RCP 1721, RCP 1711, RCP 1720 and RCP 1714). At low D-block $M_n$, $\Delta H_m$ increased sharply with D-block $M_n$, whereas at higher D-block $M_n$, $\Delta H_m$ appeared to plateau at a maximum $\Delta H_m$ of around 30-35 J/g (FIG. 10). Clearly, the poor microsphere processability, sticky character and extensive agglomeration observed for polymer-only microspheres prepared of 60CP10C20-Dxx multi-block copolymers with D-blocks of low molecular weight can be attributed to poor crystallization of the poly(p-dioxanone) pre-polymer block.

TABLE 16

Processability, average particle size (D50) and thermal characteristics (melting temperature $T_m$ and melting enthalpy) of polymer-only microspheres prepared of 60CP10C20-Dxx copolymers composed of poly(p-dioxanone) blocks of different $M_n$.

| | | $M_n$ | | Polymer | | PO-microspheres | | |
|---|---|---|---|---|---|---|---|---|
| RCP | IV (dl/g) | D-block (g/mol) | Processability | $T_m$* (° C.) | $\Delta H$* (J/g) | $D_{50}$ (μm) | $T_m$* (° C.) | $\Delta H$* (J/g) |
| 1511 | 0.89 | 1556 | Poor processability, sticky microspheres, severe agglomeration | 76.1 | 29.5 | 67.4 | 71.3 | 9.7 |
| 15116 | 0.86 | 1852 | Poor processability, sticky microspheres, severe agglomeration | 79.3 | 46.5 | 42.5 | 71.1 | 25.9 |

TABLE 16-continued

Processability, average particle size (D50) and thermal characteristics (melting temperature $T_m$ and melting enthalpy) of polymer-only microspheres prepared of 60CP10C20-Dxx copolymers composed of poly(p-dioxanone) blocks of different $M_n$.

| | | $M_n$ | | Polymer | | PO-microspheres | | |
|---|---|---|---|---|---|---|---|---|
| RCP | IV (dl/g) | D-block (g/mol) | Processability | $T_m$* (° C.) | ΔH* (J/g) | $D_{50}$ (μm) | $T_m$* (° C.) | ΔH* (J/g) |
| 1710 | 0.77 | 2116 | N.D. | 83.2 | 56.1 | — | — | — |
| 1721 | 0.80 | 2226 | Moderate processability | 83.0 | 55.2 | 74.1 | 78.3 | 32.1 |
| 1707 | 0.79 | 2269 | N.D. | 83.9 | 57.0 | — | — | — |
| 1718 | 0.78 | 2356 | N.D. | 86.3 | 56.9 | — | — | — |
| 1719 | 0.89 | 2484 | N.D. | 86.1 | 60.3 | — | — | — |
| 1711 | 0.81 | 2497 | Non sticky microspheres, no agglomeration | 85.7 | 58.0 | 50.9 | 76.2 | 32.9 |
| 1720 | 0.82 | 2575 | Non sticky microspheres, no agglomeration | 89.2 | 69.4 | 45.2 | 87.2 | 32.8 |
| 1728B | | 2538 | N.D. | 87 | 54 | — | — | — |
| 1714 | 0.81 | 2806 | Non sticky microspheres, no agglomeration | 88.3 | 63.0 | 49.3 | 87.5 | 35.8 |
| 1715 | 0.84 | 2811 | N.D. | 89.1 | 60.0 | — | — | — |
| 1812 | | 2887 | N.D. | 89 | 69 | — | — | — |
| 1807 | | 3840 | N.D. | 95 | 70 | — | — | — |

*IV is intrinsic viscosity, $M_n$ is number averaged molecular weight
*$T_m$ and ΔH of polymers were generated from $2^{nd}$ heating scan. $T_m$ and ΔH of polymer-only microspheres were determined from the total heat flow of the first heating run.

Figure 11:
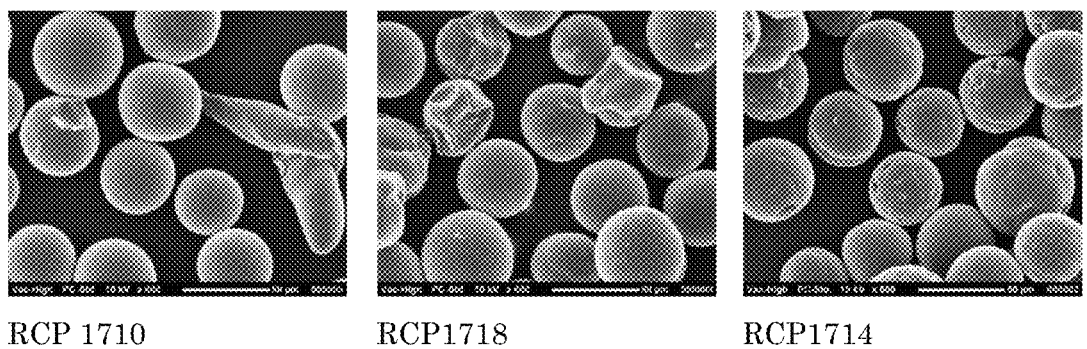
FIG. 11 SEM images polymer-only microspheres prepared of 60CP10C20-Dxx polymers containing poly(p-dioxanone) blocks with $M_n$ 2116 g/mol (RCP-1710), 2356 g/mol (RCP-1718) and 2806 g/mol (RCP-1714) (panel A) and their in vitro erosion kinetics (50CP10C20-LL40 is included as a reference) (panel B).
Figure 11:
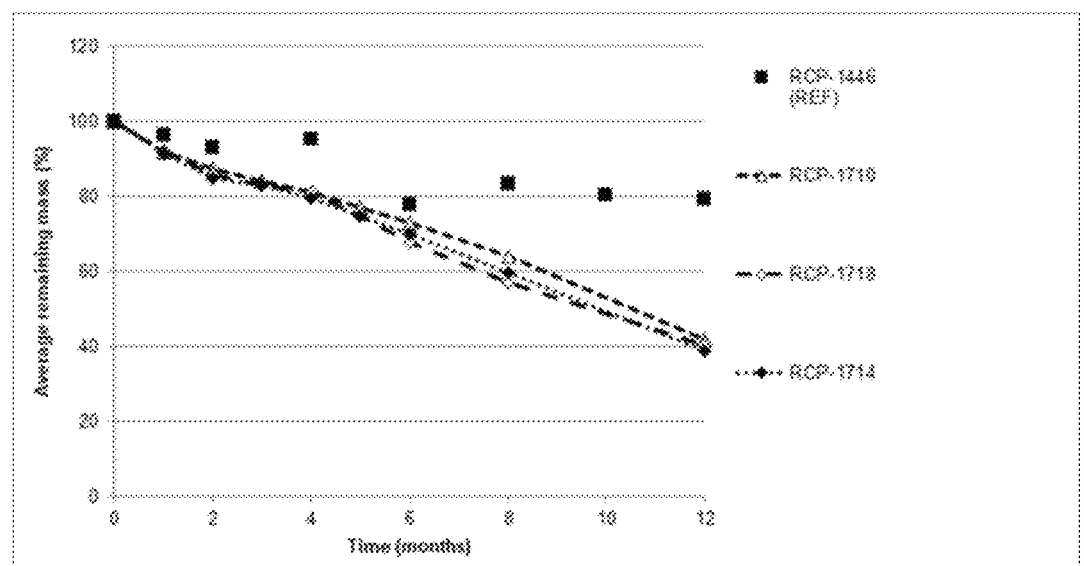

The effect of molecular weight of the poly(p-dioxanone) block on the in vitro erosion rate was studied in more detail. Polymer-only microspheres were prepared of a selection of 60CP10C20-Dxx multi-block copolymers composed of poly(p-dioxanone) blocks with molecular weights of 2116 (RCP 1710), 2356 (RCP 1718) and 2806 g/mol (RCP1714) and analysed according to the procedures described in Example 6. Spherical microspheres with a smooth surface, no visible surface porosity and an average particle size of 50 to 55 μm were obtained (FIG. 11, panel A). Thermal analysis of polymer-only microspheres was performed as described in Example 12. The melting temperature increased slightly from 81 to 88° C. with increasing D-block $M_n$ whereas the melting enthalpy was relatively constant (24-32 J/g) (Table 17). The molecular weight of the poly(p-dioxanone) blocks did not impact the in vitro erosion kinetics of microspheres 60CP10C20-Dxx-based microspheres over the range of 2100 to 2800 g/mol (FIG. 11, panel B).

TABLE 17

Thermal properties of polymer-only microsphere batches used for characterization of in vitro erosion kinetics

| MSP lot | Multi-block copolymer | RCP | $M_n$ D-block (g/mol) | $T_m$ (° C.) | $ΔH_m$ (J/g) |
|---|---|---|---|---|---|
| MS 17-068 | 60CP10C20-D21 | 1710 | 2116 | 81 | 29 |
| MS 17-069 | 6OCP10C20-D24 | 1718 | 2356 | 85 | 24 |
| MS 17-070 | 60CP10C20-D28 | 1714 | 2806 | 88 | 32 |

Example 11

In this example, sustained release microspheres were prepared for two model proteins, i.e. bovine serum albumin and lysozyme using poly(ε-caprolactone)-PEG-poly(ε-caprolactone)]-b-[poly(p-dioxanone)] multi-block copolymers with different block ratios and PEG molecular weight. The polymers were synthesised using procedures similar to those used in Example 6.

Microspheres with a target protein loading of 4.5-5 wt. % were prepared by solvent extraction/evaporation using a W1/O/W2 water-in-oil-in-water double emulsion-based membrane emulsification process. 1 g of polymer was dissolved in 9 g of dichloromethane (10.0 wt. %) and filtered over a 0.2 μm PTFE filter. Approximately 0.05 g aqueous protein solution (100 mg/ml) was added followed by emulsification using a rotor-stator mixer at 21 600 rpm for 40 seconds to yield a primary emulsion. The primary emulsion was then emulsified in 650 g of ultrapure water containing 4.0 wt. % PVA and 5 wt. % of NaCl by membrane emulsification using a membrane with 20 μm pores) to form a secondary emulsion. The secondary emulsion was stirred for 3 hours at room temperature to remove dichloromethane by solvent extraction/evaporation. The resulting microspheres were collected on a 5 μm membrane filter and washed three times with aqueous 0.05 w/v % Tween® 80 solution and three times with ultrapure water, after which the hardened microspheres were dried by lyophilisation The particle size distribution of the microspheres was measured by Coulter Counter. The BSA-loaded microspheres had an average particle size of 52 μm and a narrow particle size distribution (CV 16%), whereas the average particle size of the lysozyme-loaded microspheres was 34 μm (CV 18%). The surface morphology of the microspheres as evaluated by scanning electron microscopy according to the method described in Example 1, showed that both the BSA- and lysozyme-loaded microspheres had a smooth surface morphology without any microporosity.

Protein content of the microspheres was determined by dissolving the microspheres (5-10 mg) in 5 ml acetonitrile, followed by centrifugation, removal of 4 ml supernatant and addition of 5 ml of PBS. BSA concentration was measured by UPLC (eluent A: 0.1 wt. % TFA in UP water, eluent B: 0.1 wt. % TFA in acetonitrile. 90/10 v/v A/B to 10/90 v/v AB gradient in 4 min.

The BSA-loaded microspheres had a BSA content of 3.9% representing an encapsulation efficiency of 77%, whereas the lysozyme-loaded microspheres contained 4.6% lysozyme representing an encapsulation efficiency of 99.5%).

TABLE 18

Characteristics of BSA and lysozyme loaded microspheres prepared of 60CP10020-D26 and 20CP15050-D23 copolymers.

| Code | Protein | Polymer | Average particle size (μm) | Protein content (%) | EE (%) |
|---|---|---|---|---|---|
| SH17024 | BSA | 60CP10C20-D26 | 52(CV16%) | 3.9 | 77.0 |
| AH 17026 | Lysozyme | 20CP15C50-D23 | 34(CV18%) | 4.6 | 99.5 |

*EE = encapsulation efficiency

In, vitro release (IVR) studies of protein loaded microspheres were conducted in triplicate in 2 ml of 100 mM phosphate buffer pH 7.4 containing 0.02 w/v % NaN$_3$) thermostated at 37° C. Samples taken at pre-determined time points until completion of release were analysed with RP-UPLC to establish the cumulative protein release against sampling time.

Figure 12:
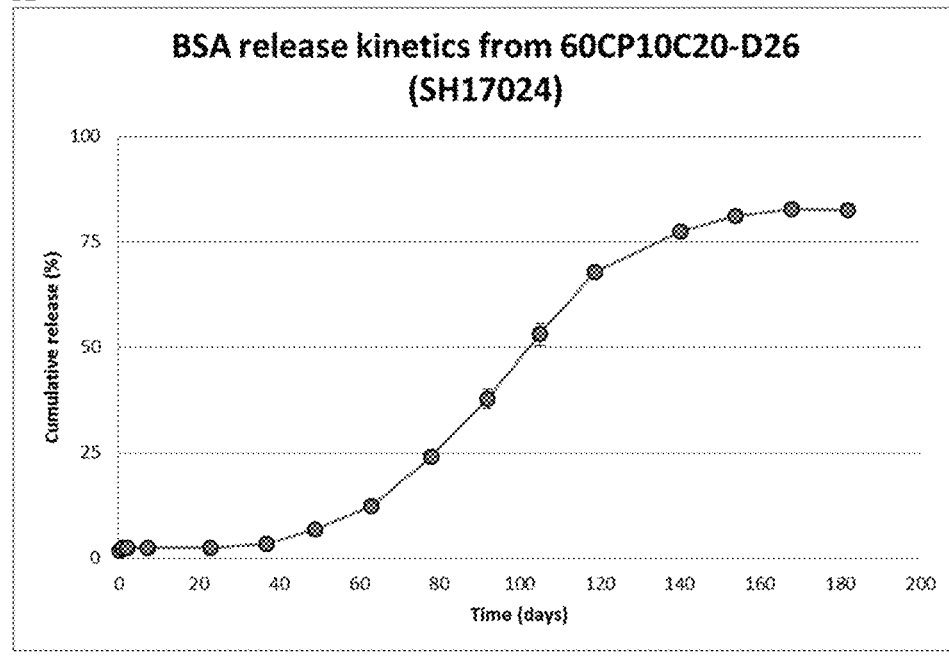
FIG. 12 Cumulative in vitro release of bovine serum albumin from 60CP10C20-D26-based microspheres (panel A) and cumulative in vitro release of lysozyme from 20CP15C50-D23-based microspheres.
Figure 12:
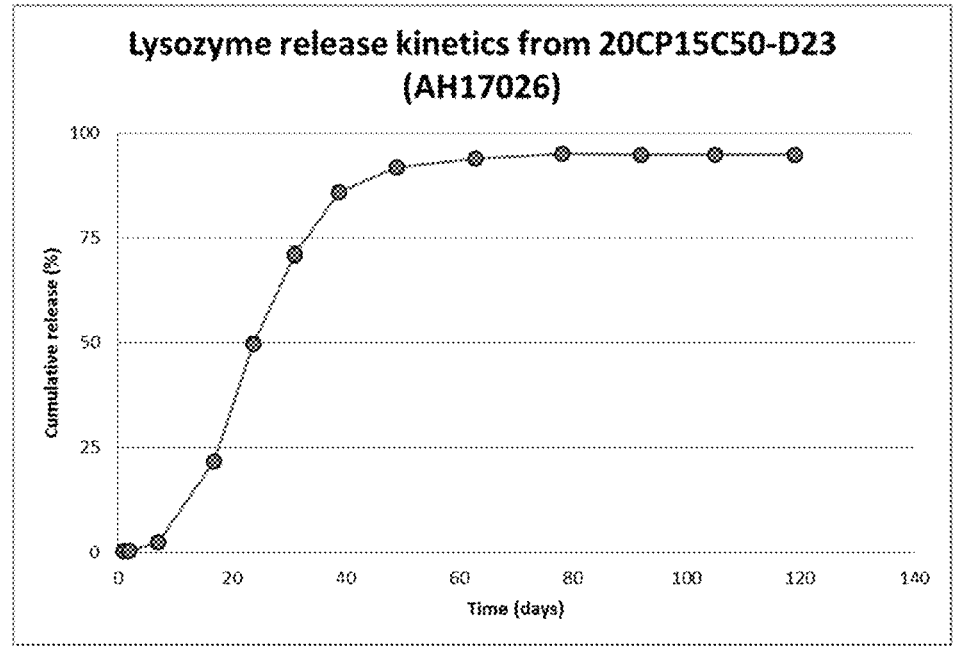

The BSA loaded 60CP10C20-D26 microspheres exhibited sigmoidal release kinetics (FIG. 12, panel A). Following a lag time of around 6 weeks during which hardly any BSA was released, BSA was released relatively linear between 2 and 4 months, after which release slowed down. The total release duration was around 5 months and the recovery was ~80%.

The lysozyme-loaded 20CP15C50-D23 microspheres also showed a lag time but only for a few days (FIG. 12, panel B). Lysozyme was released almost linearly between 1 and 6 weeks with a recovery of around 90%.

Example 12

In this example, sustained release microspheres were prepared for a 1.5 kDa peptide using [poly(ε-caprolactone)-PEG1000-poly(ε-caprolactone)]-b-[poly(p-dioxanone)] multi-block copolymers with a block ratio of 10/90 as prepared using procedures similar to those used in Example 6.

Sustained release peptide microspheres were prepared by solvent extraction/evaporation using a water-in-oil-in-water double emulsion-based membrane emulsification process. The polymer was dissolved in dichloromethane to a concentration of 10 wt. % and emulsified with an aqueous solution of the peptide yielding a primary emulsion. The primary emulsion was pumped via a membrane with 20 μm pores and into a vessel containing aqueous 4.0 wt. % PVA containing extraction medium yielding a secondary emulsion. The secondary emulsion was stirred for 3 hours at room temperature to remove DCM by solvent extraction/evaporation. The resulting microspheres were collected, washed and dried by lyophilisation.

Figure 13:
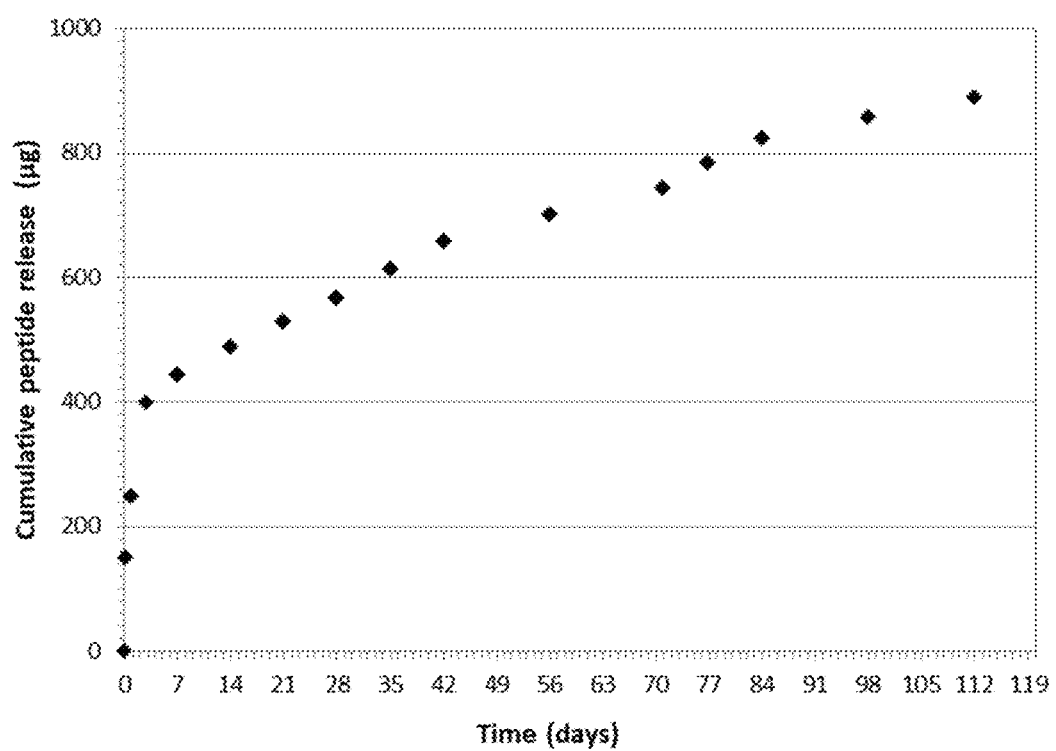
FIG. 13 Cumulative in vitro release of a 1.5 kDa peptide from microspheres composed of microspheres prepared of [poly(ε-caprolactone)-PEG1000-poly(ε-caprolactone)]-b-

The particle size distribution and the surface morphology of the microspheres were determined according to the methods described in Example 1. The peptide-loaded microspheres were spherical and had a smooth surface morphology and an average size of around 80 μm. The encapsulation efficiency was around 85%. The in vitro release kinetics of the peptide loaded microspheres were conducted in triplicate in an aqueous TRIS buffer pH 7.4 containing 0.02 w/v % NaN$_3$) at 37° C., and analysis of peptide concentration in release samples collected at predetermined time points by RP-UPLC (Waters ACQUITY UPLC BEH C18 column) using a water/acetonitrile/0.1% TFA gradient elution and UV detection at 226 nm). Following an initial burst, the peptide was slowly released thereafter at almost constant rate (FIG. 13).

Example 13

In this example, multi-block copolymers synthesised as described in Example 7 were used to prepare levonorgestrel loaded implants. Small diameter implants with a target levonorgestrel loading ranging from 20 to 48 wt. % were prepared at a scale of 7 g by hot melt extrusion using a Haake Minilab extruder. In brief, polymer and micronised levonorgestrel (D90<10 μm) were manually mixed using a spatula where after the mixture was added to the preheated extruder (100-110° C.), compounded for 5-10 minutes using a circulation loop followed by extrusion via a 0.5 mm or 1.0 mm die. After cooling down the extrudate was manually cut into implants with a length of around 10 mm.

TABLE 19

Characteristics of levonorgestrel loaded implants prepared of several poly(p-dioxanone) based multi-block copolymers and poly(DL-lactide).

| Code | Polymer | RCP | IV (dl/g) | Levonorgestrel content (wt. %) | Diameter (mm) |
|---|---|---|---|---|---|
| AD 18-009-6 (0.5) | 10LP6L12-D27 | 1804 | 0.70 | 20.8 | 0.5 |
| AD 18-009-6 (1.0) | 10LP6L12-D27 | 1804 | 0.70 | 20.8 | 1.0 |
| AD 19-003-1 (1.0) | 10LP6L12-60GL20-D27 | 1911 | 0.52 | 46.3 | 1.0 |
| AD 19-003-4 (1.0) | PDL04 (poly(DL-lactide)) | — | 0.4 | 45.5 | 1.0 |

Levonorgestrel content of the implants was determined by dissolving the implants in acetonitrile, diluting the solution with water after complete dissolution of the implant, and centrifuging down precipitated polymer. The actual contents were close to the target contents.

In vitro release (IVR) studies of levonorgestrel implants were conducted in triplicate in an aqueous-buffer (100 mM Phosphate buffer, 0.5% SDS, pH 7.4, 0.02 w/v % NaN$_3$) at 37° C. Samples were taken at pre-determined time points until completion of release and levonorgestrel concentrations were determined by RP-UPLC using a Waters ACQUITY UPLC BEH C18 column eluted with a water/acetonitrile 50/50 mixture, and detected with a UV detector (243 nm).

FIG. 14, panel B shows the cumulative in vitro release kinetics of the levonorgestrel implants. Poly(DL-lactide)- based levonorgestrel implants hardly released any levonorgestrel up to four months. 10LP6L12-D27-based levonorgestrel implants showed sustained release with a duration of up to 3 months (0.5 mm) or 4 months (1.0 mm). Levonorgestrel implants composed of 10LP6L12-60GL20-D27 showed almost completely linear release kinetics from the start up to 3 months. At the 3 months' time point it was noticed that hardly any remnants of the 10LP6L12-D27- and 10LP6L12-60GL20-D27-based implants were left indicating that the polymers had completely degraded by then.

The invention claimed is:

1. A biodegradable, phase separated, thermoplastic multi-block copolymer comprising at least one amorphous hydrolysable pre-polymer (A) segment and at least one semi-crystalline hydrolysable pre-polymer (B) segment; wherein
said multi-block copolymer under physiological conditions has a $T_g$ of 37° C. or less and a $T_m$ of 50-110° C.,
said pre-polymer (A) and (B) segments are linked by a multifunctional chain-extender,
said pre-polymer (A) and (B) segments are randomly distributed over the multi-block copolymer, and
said pre-polymer (B) segment comprises a X-Y-X tri-block copolymer, wherein
Y is a polymerisation initiator and
X is a poly(p-dioxanone) segment with a block length expressed in p-dioxanone monomer units of 7 or more.

2. The biodegradable, phase separated, thermoplastic multi-block copolymer of claim 1, wherein X is a poly(p-dioxanone) segment with a block length expressed in p-dioxanone monomer units of 7-35.

3. The biodegradable, phase separated, thermoplastic multi-block copolymer of claim 1, wherein said pre-polymer (B) segment has a ratio of weight average molecular weight over number average molecular weight $(M_w/M_n)$ of 1.0-3.0.

4. The biodegradable, phase separated, thermoplastic multi-block copolymer of claim 1, wherein at least part of said pre-polymer (A) segment is derived from a water-soluble polymer.

5. The biodegradable, phase separated, thermoplastic multi-block copolymer of claim 1, wherein 30% or more by total weight of said pre-polymer (A) segment is derived from a water-soluble polymer.

6. The biodegradable, phase separated, thermoplastic multi-block copolymer of claim 1, wherein said pre-polymer (A) segment comprises poly(p-dioxanone).

7. The biodegradable, phase separated, thermoplastic multi-block copolymer of claim 6, wherein 80% or less by total weight of said pre-polymer (A) segment is poly(p-dioxanone).

8. The biodegradable, phase separated, thermoplastic multi-block copolymer of claim 1, wherein 70% or more by total weight of said pre-polymer (B) segment is poly(p-dioxanone).

9. The biodegradable, phase separated, thermoplastic multi-block copolymer of claim 1, wherein said pre-polymer (B) segment has a number average molecular weight $(M_n)$ of 1300-7200 g/mol.

10. The biodegradable, phase separated, thermoplastic multi-block copolymer of claim 1, wherein said pre-polymer (B) segment has a weight average molecular weight $(M_w)$ of 1800-10,080 g/mol.

11. The biodegradable, phase separated, thermoplastic multi-block copolymer of claim 1, wherein said pre-polymer (B) segment has a $T_g$ of less than 0° C.

12. The biodegradable, phase separated, thermoplastic multi-block copolymer of claim 1, wherein said pre-polymer (B) segment has a $T_m$ in the range of 60-100° C.

13. The biodegradable, phase separated, thermoplastic multi-block copolymer of claim 4, wherein said water-soluble polymer comprises one or more polyethers selected from the group consisting of polyethylene glycol (PEG), polytetramethyleneoxide (PTMO), and polypropyleneglycol (PPG), or one or more water-soluble polymers selected from the group consisting of polyvinylalcohol (PVA), polyvinylpyrrolidone (PVP), polyvinylcaprolactam, poly(hydroxyethylmethacrylate)(poly-(HEMA)), and polyphosphazenes, or copolymers of any of these polymers.

14. The biodegradable, phase separated, thermoplastic multi-block copolymer of claim 4, wherein said water-soluble polymer is derived from poly(ethylene glycol) (PEG) having a number average molecular weight $(M_n)$ of 150-5000 g/mol.

15. The biodegradable, phase separated, thermoplastic multi-block copolymer of claim 1, wherein said chain-extender is a difunctional aliphatic chain-extender.

16. The biodegradable, phase separated, thermoplastic multi-block copolymer of claim 15, wherein said difunctional aliphatic chain-extender is a diisocyanate.

17. The biodegradable, phase separated, thermoplastic multi-block copolymer of claim 1, wherein said pre-polymer (A) segment comprises reaction products of cyclic monomers and/or non-cyclic monomers;
wherein said non-cyclic monomers are at least one selected from the group consisting of succinic acid, glutaric acid, adipic acid, sebacic acid, lactic acid, glycolic acid, hydroxybutyric acid, ethylene glycol, diethylene glycol, 1,4-butanediol and 1,6-hexanediol and
wherein said cyclic monomers are at least one selected from the group consisting of glycolide, lactide, ε-caprolactone, δ-valerolactone, trimethylene carbonate, tetramethylenecarbonate, 1,5-dioxepane-2-one, 1,4-dioxane-2-one (p-dioxanone) and cyclic anhydrides.

18. The biodegradable, phase separated, thermoplastic multi-block copolymer of claim 1, further comprising a water-soluble polymer as an additional pre-polymer.

19. The biodegradable, phase separated, thermoplastic multi-block copolymer of claim 18, wherein said additional pre-polymer is 30% or less by total weight of the multi-block copolymer.

20. The biodegradable, phase separated, thermoplastic multi-block copolymer of claim 1, being a poly (ether ester) multi-block copolymer,
wherein said pre-polymer (A) segment comprises one or more selected from the group consisting of

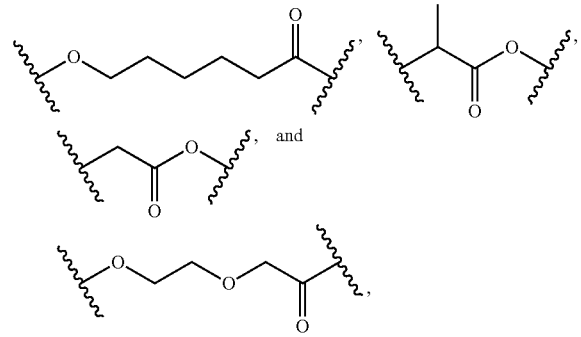

and further comprises

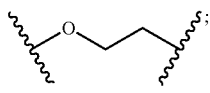 [SMILES: *CCO*]

and
wherein said pre-polymer (B) segment comprises

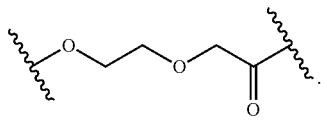 [SMILES: *OCCOCC(*)=O]

21. The biodegradable, phase separated, thermoplastic multi-block copolymer of claim 1, wherein said pre-polymer (A) segment is represented by

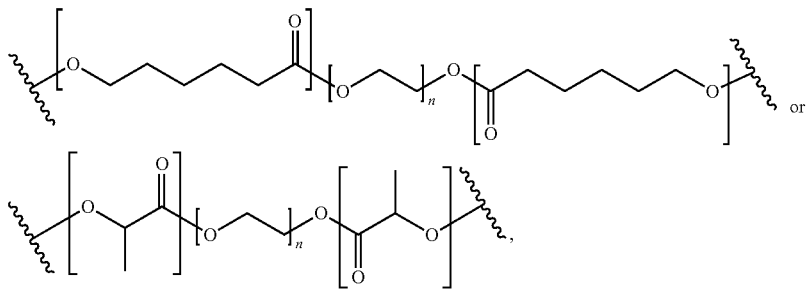

and n is 4-120.

22. The biodegradable, phase separated, thermoplastic multi-block copolymer of claim 1, which is represented by $[(R^1R^2{}_nR^3)_q]_r[(R^4{}_pR^5R^6{}_p)]_s$, wherein
R$^1$ and R$^3$ are independently selected from the group consisting of

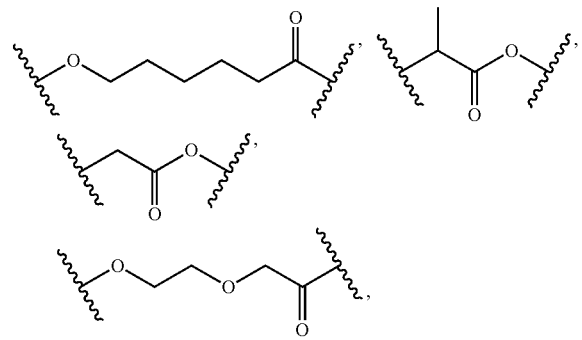

and any combination thereof;
R$^2$ is

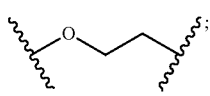

R$^4$ and R$^6$ are each

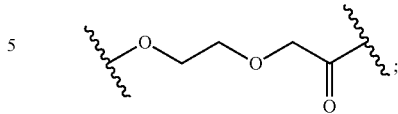

n is a number of repeating R$^2$ moieties of 4-120;
p is a number of repeating R$^4$ and R$^6$ moieties of 7 or more;
q is a number average molecular weight of $(R^1R^2{}_nR^3)$ of 400-10,000 g/mol; and
r/s is a pre-polymer (A) segment over pre-polymer (B) segment ratio of 0.1-2.5.

23. The biodegradable, phase separated, thermoplastic multi-block copolymer of claim 1, which is formed as microspheres.

24. A process for preparing the biodegradable, phase separated, thermoplastic multi-block copolymer of claim 1, the process comprising either:

performing a chain-extension reaction using a multifunctional chain-extender, wherein said pre-polymer (A) and (B) segments are both diol or diacid terminated and the chain-extender is di-carboxylic acid, diisocyanate, or diol terminated; or performing a chain-extension reaction using a coupling agent, wherein said pre-polymer (A) and (B) segments are both diol or diacid terminated and the coupling agent is dicyclohexyl carbodiimide.

25. A method of delivering a drug to a host, comprising administering the drug encapsulated in a matrix to the host, wherein said matrix comprises at least one biodegradable, semi-crystalline, phase separated, thermoplastic multi-block copolymer of claim 1.

26. A composition for delivery of at least one biologically active compound to a host, comprising at least one biologically active compound encapsulated in a matrix, wherein said matrix comprises at least one biodegradable, semi-crystalline, phase separated, thermoplastic multi-block copolymer of claim 1.

27. The composition of claim 26, wherein said at least one biologically active compound is a non-peptide non-protein small sized drug, or a biologically active polypeptide.

28. The biodegradable, phase separated, thermoplastic multi-block copolymer of claim 1, wherein X is a poly(p-dioxanone) segment with a block length expressed in p-dioxanone monomer units of 11-14.

29. The biodegradable, phase separated, thermoplastic multi-block copolymer of claim 1, wherein said pre-polymer (B) segment has a number average molecular weight ($M_n$) of 2200-3200 g/mol.

30. The biodegradable, phase separated, thermoplastic multi-block copolymer of claim 1, wherein said pre-polymer (B) segment has a weight average molecular weight ($M_w$) of 3000-4200 g/mol.

* * * * *